United States Patent [19]
Kriegler et al.

[11] Patent Number: 5,998,378
[45] Date of Patent: Dec. 7, 1999

[54] COMPOSITIONS FOR THE INHIBITION OF TNF HORMONE FORMATION AND USES THEREOF

[75] Inventors: Michael Kriegler, Rancho Santa Fe; Carl Perez, San Diego; Robert F. Halenbeck, San Rafael; David A. Jewell, Sausalito; Kirston E. Koths, El Cerrito, all of Calif.

[73] Assignee: Chiron Corporation, Emeryville, Calif.

[21] Appl. No.: 08/230,428

[22] Filed: Apr. 19, 1994

Related U.S. Application Data

[63] Continuation of application No. 07/905,546, Jun. 25, 1992, abandoned, which is a continuation-in-part of application No. 07/395,253, Aug. 16, 1989, abandoned.

[51] Int. Cl.$^6$ ..................................................... A61K 38/00
[52] U.S. Cl. ........................... 514/18; 530/331; 530/351; 530/388.23; 530/389.2; 424/85.1; 424/145.1; 424/158.1
[58] Field of Search ................................ 435/5, 7.1, 7.2, 435/7.21, 7.23, 7.24, 23, 184, 218, 226; 436/501, 503, 504, 811; 514/18, 457; 424/85.1, 85.8, 88, 145.1, 158.1, 152.1, 146.1, 198.1; 530/331, 350, 351, 388.23, 389.2

[56] References Cited

U.S. PATENT DOCUMENTS

| | | | |
|---|---|---|---|
| 4,179,337 | 12/1979 | Davis et al. | |
| 4,495,285 | 1/1985 | Shimizu et al. | |
| 4,582,788 | 4/1986 | Ehrlich | 435/6 |
| 4,596,822 | 6/1986 | Powers et al. | 435/184 |
| 4,609,546 | 9/1986 | Hiratani | |
| 4,677,063 | 6/1987 | Mark et al. | 435/69.5 |
| 4,677,064 | 6/1987 | Mark et al. | 435/69.1 |
| 4,683,195 | 7/1987 | Mullis et al. | 435/6 |
| 4,683,202 | 7/1987 | Mullis | 435/91 |
| 4,699,904 | 10/1987 | Doherty et al. | |
| 4,704,692 | 11/1987 | Ladner | |
| 4,711,886 | 12/1987 | Finke et al. | |
| 4,717,722 | 1/1988 | Doherty et al. | |
| 4,766,106 | 8/1988 | Katre et al. | |
| 4,797,396 | 1/1989 | Finke et al. | 514/210 |
| 4,816,567 | 3/1989 | Cabilly et al. | |
| 4,829,054 | 5/1989 | Emerson et al. | 514/21 |
| 4,923,807 | 5/1990 | Webb et al. | 435/69.2 |
| 4,968,614 | 11/1990 | Takiguchi et al. | 435/172.3 |
| 5,091,303 | 2/1992 | Arnaout et al. | 435/7.24 |
| 5,109,018 | 4/1992 | Powers et al. | 514/457 |
| 5,124,147 | 6/1992 | Wissner et al. | 424/85.8 |
| 5,128,258 | 7/1992 | Klostergaard | 435/240.2 |
| 5,136,021 | 8/1992 | Dembinski et al. | 530/350 |
| 5,180,819 | 1/1993 | Cayre et al. | 536/23.2 |
| 5,200,333 | 4/1993 | Wilson | 435/172.3 |
| 5,247,070 | 9/1993 | Yamamada et al. | 530/351 |

FOREIGN PATENT DOCUMENTS

| | | |
|---|---|---|
| 2020700 | 2/1991 | Canada . |
| 146026 | 6/1985 | European Pat. Off. . |
| 148311 | 7/1985 | European Pat. Off. . |
| 155549 | 9/1985 | European Pat. Off. . |
| 158286 | 10/1985 | European Pat. Off. . |
| 168214 | 1/1986 | European Pat. Off. . |
| 174204 | 3/1986 | European Pat. Off. . |
| 0 260 610 B1 | 3/1988 | European Pat. Off. . |
| 268110 | 5/1988 | European Pat. Off. . |
| 270799 | 6/1988 | European Pat. Off. . |
| 0 288 088 B1 | 10/1988 | European Pat. Off. . |
| 0 308 378 B1 | 3/1989 | European Pat. Off. . |
| 0 395 254 A2 | 10/1990 | European Pat. Off. . |
| 0 398 327 B1 | 11/1990 | European Pat. Off. . |
| 171496 B1 | 5/1993 | European Pat. Off. . |
| 62-100291 | 8/1984 | Japan . |
| 2177096 | 9/1985 | United Kingdom . |
| 2158829 | 11/1985 | United Kingdom . |
| 2188638 | 3/1986 | United Kingdom . |
| WO 91/02540 | 3/1991 | WIPO . |
| WO 91/09865 | 7/1991 | WIPO . |
| WO 92/00378 | 1/1992 | WIPO . |
| WO 93/07171 | 4/1993 | WIPO . |
| WO 93/16698 | 9/1993 | WIPO . |
| WO 94/00555 | 1/1994 | WIPO . |
| WO 95/02579 | 1/1995 | WIPO . |

OTHER PUBLICATIONS

Abstract, Dialog Accession No. 06706182, Medline Accession No. 89008182, Oshawa F. et al.: "Selective degradation of tumor necrosis factor in sensitive cells, and production of membrane–active substance"; and *J. Biochem.* (Tokyo) (Japan) (Apr. 1988) 103(4): 730–4.

Williams et al., "Epitope on Proteinase–3 Recognized by Antibodies from Patients with Wegener's Granulomatosis," *J. of Immunol.*, 152:4722–4737 (1994).

Witko–Sarsat et al., "Expression of Recombinant Proteinase 3—Implication for its Role as Autoantigen," *Clin. Exp. Immunol.*, 101:40 (1995) (Abstract 23).

Zimmer et al., "Three Human Elastase–Like Genes Corrdinately Expressed in the Myelomonocyte Lineage are Organized as a Small Genetic Locus on 19pter," *Proc. Nat'l Acad. Sci.*, USA, 89:8215–8219 (Sep., 1992).

Lüdemann et al., "Anti–Neutrophil Cytoplasm Antibodies in Wegener's Granulomatosis Recognize an Elastinolytic Enzyme," *J. Exp. Med.*, 171:357–362 (Jan., 1990).

Lüdemann et al., "Detection and Quantitation of Anti–meutrophil Cytoplasm Antibodies in Wegener's Granulomatosis by ELISA Using Affinity–purified Antigen," *J. Immun. Meth.*, 114:167–174 (1988).

*Primary Examiner*—Christina Y. Chan
*Assistant Examiner*—Patrick J. Nolan
*Attorney, Agent, or Firm*—McAndrews, Held & Malloy, Ltd.; Kimberlin L. Morley; Robert P. Blackburn

[57] ABSTRACT

Compounds having proteolytic inhibitory activity useful for treating diseases, particularly as applied to the treatment of sepsis, AIDS or autoimmune diseases, resulting from a decrease in the circulating level of mature protein hormones derived from the proteolytic cleavage of prohormone precursors such as 26 kDProTNF, and methods for identifying compounds having the desired inhibitory activity are provided.

14 Claims, 11 Drawing Sheets

OTHER PUBLICATIONS

Maiorella et al., "Large–Scale Insect Cell–Culture for Recombinant Protein Production," *Bio/Technology,* 6:1406–1410 (Dec., 1988).

Marks et al., "Enkephalin Analogs as Substrates for the Assay of Brain Cysteine Proteinase (Cathepsin L) and its Endogenous Inhibitors," *Peptides,* 10:391–394 (1989).

McGuire et al., "Generation of Active Myeloid and Lymphoid Granule Serine Proteases Requires Processing of the Granule Thiol Protease Dipeptidyl Peptidase I," *J. Biol. Chem.,* 268(4):2458–2467 (Feb. 5, 1993).

Merril et al., "Interleukin–1 and Tumor Necrosis Factor α Can Be Induced from Mononuclear Phagocytes by Human Immunodeficiency Virus Type 1 Binding to the CD4 Receptor," *J. Virol.,* 63(10):4404–4408 (Oct., 1989).

Mohler et al., "Protection Against a Lethal Dose of Endotoxin by an Inhibitor of Tumour Necrosis Factor Processing," *Nature,* 370:218–220 (Jul. 21, 1994).

Mullis et al., "Specfic Enzymatic Amplification of DNA In Vitro: The Polymerase Chain Reaction," *Cold Spring Harbor Symposium Quant. Biol.,* Cold Spring Harbor Laboratory, vol. LI, pp. 263–273 (1986).

Müller et al., "Synthesis and maturation of recombinant human tumor necrosis factor in eukaryotic systems," *FEBS 3424,* 197(1,2):99–104 (Mar., 1986).

Muller–Bérat et al., "The Phylogeny of Proteinase 3/Myeloblastin, and Myeloperoxidase as Shown by Immunohistochemical Studies on Human Leukemic Cell Lines," *Clin. Exp. Immunol.,* 93:24 (1993) (Abstract 31).

Munemitsu et al., "Molecular Cloning and Expression of a G25K cDNA, the Human Homolog of the Yeast Cell Cycle Gene CDC42," *Mol. Cell. Biol.,* 10(11):5977–5982 (Nov., 1988).

Niles et al., "Wegener's Granulomatosis Autoantigen is a Novel Neutrophil serine Proteinase," *Blood,* 74(6):1888–1893 (Nov. 1, 1989).

Nowotny et al., "Preparation and Activity Measurements of Deuterated 50S Subunits for Neuron–Scattering Analysis," *Methods in Enzymology,* 164:131–147 (1988).

Olsen et al., "High–Efficiency Oligonucleotide–Directed Plasmid Mutagenesis," *Proc. Nat'l Acad. Sci., USA,* 87:1451–1455 (Feb., 1990).

Poli et al., "Tumor Necrosis Factor α Functions in an Autocrine Manner in the Induction of Human Immunodeficiency Virus Expression," *Proc. Nat'l Acad. Sci., USA,* 87:782–785 (Jan., 1990).

Robache–Gallea et al., "In Vitro Processing of Human Tumor Necrosis Factor–α," *J. Biol. Chem.,* 270(40):23688–23692 (Oct. 6, 1995).

Salvesen et al., "An Unusual Specificity in the Activation of Neutrophil Serine Proteinase Zymogens," *Biochem.,* 29:5304–5308 (1990).

Salvesen et al., "Zymogen Activation Specificity and Genomic Structure of Human Neutrophil Elastase and Cathepsin G Reveal a New Branch of the Chymotrypsinogen Superfamily of Serine Proteinases," *Biomed. Biochim. Acta,* 50:665–671 (1991).

Savige et al., "Anti–Neutrophil Cytoplasmic Antibodies (ANCA): Their Detection and Significance: Report from Workshops," *Pathology,* 26:186–193 (1994).

Seckinger et al., "A Human Inhibitor of Tumor Necrosis Factor α," *J. Exp. Med.* 167:1511–1516 (Apr., 1988).

Smith et al., "Production of Human Beta Interferon in Insect Cells Infected with a Baculovirus Expression Vector," *Mol. Cell. Biol.,* 3(12)2156–2165 (Dec., 1983).

Streiter et al., "Cellular and Molecular Regulation of Tumor Necrosis Factor–Alpha Production by Pentoxifylline," *Bioch. Biophys. Res. Comm.,* 155(3):1230–1236 (Sep. 30, 1988).

Sturrock et al., "Structure, Chromosomal Assignment, and Expression of the Gene for Proteinase–3," *J. Biol. Chem.,* 267(29):21193–21199 (Oct. 15, 1992).

Summers and Smith, A Manual of Methods for Baculovirus Vectors and Insect Cell Culture Procedures, *Texas Agrigultural Experiment Station, Bulletin No. 1555,* pp. 1–56 (May, 1987).

Takahashi et al., "Structure of the Human Neutrophil Elastase Gene," *J. Biol. Chem.,* 263(29):14739–14747 (Oct. 15, 1988).

Takebe et al., "SRα Promoter: an Efficient and Versatile Mammalian cDNA Expression System Composed of the Simian Virus 40 Early Promoter and the R–U5 Segment of Human T–Cell Leukemia Virus Type 1 Long Terminal Repeat," *Mol. Cell Biol.,* 8(1):466–472 (Jan., 1988).

Urata et al., "Dipeptide Processing Activates Recombinant Human Prochymase," *J. Biol. Chem.,* 268(32):24318–24322 (Nov. 15, 1993).

White and Littman, "Viral Receptors of the Immunoglobulin Superfamily," *Cell,* 56:725–728 (Mar. 10, 1989).

Fazely et al., "Pentoxifylline (Trental) Decreases the Replication of the Human Immunodeficiency Virus Type I in Human Peripheral Blood Mononuclear Cells and in Cultured T Cells," *Blood,* 77(8):1653–1656 (Apr. 15, 1991).

Fiers, W., "Tumor Necrosis Factor: Characterization at the Molecular, Cellular and In Vivo Level," *FEB 09976,* 285(2):199–212 (Jul., 1991).

Gabay et al., "Antibiotic Proteins of Human Polymorphonuclear Leukocytes," *Proc Nat'l Acad, Sci,* USA, 86:5610–5614 (Jul., 1989).

Goodwin et al., "Molecular and Biological Characterization of a Ligand for CD27 Defines a New Family of Cytokines with Homology to Tumor Necrosis Factor," *Cell,* 73:447–456 (May 7, 1993).

Graf et al., "Cloning of TRAP, a Ligand for CD40 on Human T Cells," *Eur. J. Immunol.,* 22:3191–3194 (1992).

Gupta et al., "Identity of Wegener's Autoantigen (P29) with Proteinase 3 and Myeloblastin," *Blood,* 76(10):2162 (Nov. 15, 1990).

Hagen, E.C., "Standardisation of ANCA Assays Using Purified Proteinase–3 (PR–3) and Myeloperoxidase (MPO)," *Clin. Exp. Immunol.,* 101:41 (1995) (Abstract 27).

Hinshaw et al., "Survival of Primates in $LD_{100}$ Septic Shock Following Therapy With Antibody to Tumor Necrosis Factor (TNFα)," *Circulatory Shock,* 30:279–292 (1989).

Henshaw et al., "Elevations of Neutrophil Proteinase 3 In Serum of Patients with Wegener's Granulomatosis and Polyarteritis Nodosa," *Arthritis and Rheumatism,* 37(1):104–112 (1994).

Howard et al., "Soluble Tumor Necrosis Factor Receptor: Inhibition of Human Immunodeficiency Virus Activation," *Proc. Nat'l Acad. Sci.,* USA, 90:2335–2339 (Mar., 1993).

Huang et al., "Epitope Mapping on the Proteinase 3 Molecule Using Monoclonal Antibodies and Sera From Patients with Wegener's Granulomatosis," *Clin. Exp. Immunol.,* 101:50 (1995) (Abstract 64).

Ito et al., "Tumor Necrosis Factor Antagonizes Inhibitory Effect of Azidothymidine on Human Immunodeficiency Virus (HIV) Replication In Vitro," *Bioch. Biophys. Res. Comm.,* 166(3):1095–1101 (Feb. 14, 1990).

Jarvis et al., "Influence of Different Signal Peptides and Prosequences on Expression of Secretion of Human Tissue Plasminogen Activator in the Baculovirus System," *J. Biol. Chem.,* 268(22):16754–16762 (Aug. 5, 1993).

Jennette and Falk, "Clinical and Pathological Classification of ANCA–associated Vasculitis: What Are the Controversies?," *Clin. Exp. Immunol.,* 101:18–21 (1995).

Jennings et al., "Anti–Poteinase 3 Antibodies, Their Characterization and Disease Associations," *Clin. Exp. Immunol.,* 95:251–256 (1994).

Kallenberg et al., "Antineutrophil Cytoplasmic Antibodies: A Still–Growing Class of Autoantibodies in Inflammatory Disorders," *Am. J. of Med.,* 93:675–682 (Dec., 1992).

Kallenberg et al., "ELISA for the Detection of Antibodies Against Neutrophil Cytoplasm Antigens," *Techniques in Diagnostic Pathology,* 2:49–60 (1991).

Kao et al., "Proteinase 3: A Distinct Human Polymorphonuclear Leukocyte Proteinase that Produces Emphysema in Hamsters," *J. Clin. Invest.,* 82:1963–1973 (Dec., 1988).

Kitts et al., "Linearization of Baculovirus DNA Enhances the Recovery of Recombinant Virus Expression Vectors", *Nucleic Acids Res.,* 18(19):5667–5672 (1990).

Kriegler et al., "Gene Transfer and Expression," Stockton Press, pp. 99–100, 114–135 (1990).

Lähdevirta et al., "Elevated Levels of Circulating Cachetin/Tumor Necrosis Factor in Patients with acquired Immunodeficiency Syndrome," *Am. J. Med.,* 85:289–291 (Sep., 1988).

Lau et al., "Regulation of Tumor Necrosis Factor Receptor Expression by Acid–Labile Interferon–α from AIDS Sera," *AIDS Res. Hum. Retroviruses,* 7(6):545–552 (1991).

Lau and Livesay, "Endotoxin Induction of Tumor Necrosis Factor Is Enhanced by Acid–labile Interferon–α in Acquired Immunodeficiency Syndrome," *J. Clin. Invest.,* 84:738–743 (Sep., 1989).

Lawton et al., "Anti–Proteinase 3 Antibody in Hong Kong Chinese," *Clin. Exp. Immunol.,* 101:72 (1995) (Abstract 152).

Lebouille et al., "Properties of a Leu–Phe–Cleaving Endopeptidase Activity Putatively Involved in β–Endorphin Metabolism in Rat Brain," *J. Neurochem.,* 52:1714–1721 (1989).

Leid et al., "Cleavage and Inactivation of Human C1–Inhibitor by the Human Leukocyte Proteinase, Proteinase 3," *Clin. Exp. Immunol.* 93:24 (1993).

Luben and Mohler, "In Vitro Immunization as an Adjunct to the Production of Hybridomas Producing Antibodies Against the Lymphokine Osteoclast Activating Factor," *Molecular Immunology,* 121:635–639 (1980).

Berger et al., "The Neutrophil Enzymes Proteinase 3 and Elastase Enhance the Production of IL–8 by Endothelial Cells in Culture," *Clin. Exp. Immunol.,* 101(Supplement 1):35 (1995) (Abstract 1).

Bini et al., "Antineutrophil Cytoplasm Autoantibodies in Wegener's Granulomatosis Recognize Conformational Epitopes on Proteinase 3," *J. of Immunol.,* 149(4):1409–1415 (Aug. 15, 1992).

Brakch et al., "Processing Endoprotease Recognizes a Structural Feature at the Cleavage Site of Peptide Prohormones," *J. Biol. Chem.,* 264(27):15912–15916 (Sep. 25, 1989).

Brown et al., "Dipeptidyl Peptidase I Is Enriched in Granules of in Vitro– and in Vivo–Activated Cytotoxic T Lymphocytes," *J. of Immunol.,* 150(11):4733–4742 (Jun 1, 1993).

Buchan et al., "Interleukin–1 and Tumor Necrosis Factor mRNA Expression in Rheumatoid Arthritis: Prolonged Production of IL–1α," *Clin. Exp. Immunol.,* 73:449–455 (1988).

Buetler et al., "Cachectin and Tumor Necrosis Factor as Two Sides of the Same Biological Coin," *Nature,* 320:584–588 (Apr. 17, 1986).

Caputo et al., "Activation of Recombinant Murine Cytotoxic Cell Proteinase–1 Requires Deletion of an Amino–terminal Dipeptide," *J. of Biol. Chem.,* 268(24):17672–17675 (Aug. 25, 1993).

Carswell et al., "An Endotoxin–Induced Serum Factor That Causes Necrosis of Tumors," *Proc. Nat'l Acad. Sci.,* USA, 72(9):3666–3670 (Sep., 1975).

Castro et al., "1993 Revised Classification System for HIV Infection and Expanded Surveillance Case Definition for AIDS Among Adolescents and Adults," *Morbid. Mortal. Wk. Rep.,* 41(RR–17):1–19 (Dec. 18, 1993).

Chang et al., "Epitope Mapping of Anti–Proteinase 3 and Anti–Myeloperoxidase Antibodies," *Clin. Exp. Immunol.,* 102:112–119 (1995).

Chang et al., "B Cell Epitope Mapping of Anti–Proteinase 3 and Anti–Myeloperoxidase Antibodies," *Clin. Exp. Immunol.,* 101:51 (1995) (Abstract 66).

Chu et al., "Localization of Tumor Necrosis Factor α in Synovial Tissues and at the Cartilage–Pannus Junction in Patients with Rheumatoid Arthritis," *Arthritis and Rheumatism,* 34(9):1125–1131 (Sep., 1991).

Dalboge et al., "A Novel Enymatic Method for Production of Authentic hGH from an *Escherichia Coli* Produced hGH–Precursor," *Bio/Technology,* 5:161–164 (Feb., 1987).

Dalpé et al., "The Conformational Determinants Recognized by Wegener's C–ANCAS are Situated at or Near the Catalytic Domain of Myeloblastin," *Clin. Exp. Immunol.,* 93:21 (1993) (Abstract 19).

DeStefano et al., "Acid–Labile Human Leukocyte Interferon in Homosexual Men with Kaposi's Sarcoma and Lymphadenopathy," *J. Inf. Dis.,* 146(4):451–455 (Oct., 1982).

Dezube et al., "Pentoxifylline Decreases Tumor Necrosis Factor Expression and Serum Triglycerides in People with AIDS," *J. Acq. Immune Def. Syndrome,* 6:787–794 (1993).

Di Marco et al., "Purification, Analysis, and Enzymatic Activity of Recombinant Human Synovial Fluid Phospholipase $A_2$ and N–Terminal Variants," *J. Biochem.,* 112:350–354 (1992).

Duffaud et al., "Signal Peptidases Recognize a Structural Feature at the Cleavage Site of Secretory Proteins," *J. Biol. Chem.,* 263(21):10224–10228 (Jul. 25, 1988).

Duh et al., "Tumor Necrosis Factor α Activates Human Immunodeficiency Virus Type 1 Through Induction of Nuclear Factor Binding to the NF–kB Sites in the Long Terminal Repeat," *Proc. Nat'l Acad. Sci.,* USA, 86:5974–5978 (Aug., 1989).

Eyster et al., "Acid–Labile Alpha Interferon: A Possible Preclinical Marker for the Acquired Immunodeficiency Syndrome in Hemophilia," *N. Eng. J. Med.,* 309(10):583–586 (1983).

Maxam et al., "Sequencing End–Labeled DNA with Base–Specific Chemical Cleavages", *Meth. Enzym.,* 65:499–560 (1980).

Merrifield, "Solid Phase Synthesis", *Science,* 232:341–347 (1986).

Messing et al., "A system for shotgun DNA sequencing", *Nucleic Acids Res.,* 9:309–321 (1981).

Navia et al., "Structure of human neutrophil elastase in complex with a peptide chloromethyl ketone inhibitor at 1.84-Å resolution", *PNAS(USA),* 86:7–11 (1989).

Rao et al., "Characterization of Proteinase-3 (PR-3), a Neutrophil Serine Proteinase", *J. Biol. Chem.,* 266:9540–9548 (1991).

Reading, "Theory and Methods for Immunization in Culture and Monoclonal Antibody Production", *J. of Immun. Methods,* 53:261–291 (1982).

Reading, "In Vitro Immunization for the Production of Antigen–Specific Lymphocyte Hybridomas", *Meth. Enzym.,* 121:18–27 (1986).

Roder et al., "The EBV–Hybridoma Technique", *Meth. Enzym.,* 121:140–167 (1986).

Sanger et al., "DNA sequencing with chain–terminating inhibitors", *PNAS(USA),* 74:5463–5467 (1977).

Schlom et al., "Generation of human monoclonal antibodies reactive with human mammary carcinoma cells", *PNAS(USA),* 77:6841–6845 (1980).

Scuderi, "Cathepsin–G and Leukocyte Elastase Inactivate Human Tumor Necrosis Factor and Lymphotoxin", *Cellular Immun.,* 135:299–313 (1991).

Seckinger et al., "Purification and Biologic Characterization of a Specific Tumor Necrosis Factor α Inhibitor", *J. Biol. Chem.,* 264:11966–11973 (1989).

Seckinger et al., "A Human Inhibitor of Tumor Necrosis Factor α", *J. Exp. Med.,* 167:1511–1516 (1988).

Smith, "In Vitro Mutagenesis", *Annual Review of Genetics,* 19:423–462 (1985).

Springer, "Cell–Surface Differentiation in the Mouse", *Monoclonal Antibodies,* 194 (Eds. Kennett, T. McKearn & K. Bechtol, Plenum Press, NY (1980).

Stetler et al., "Isolation and sequence of a human gene encoding a potent inhibitor of leukocyte proteases", *Nucleic Acids Research,* 14:7883–7896 (1986).

Tracey et al., "Anti–cachectin/TNF monoclonal antibodies prevent septic shock during lethal bacteraemia", *Nature,* 330:662–664 (1987).

Wigler et al., "Biochemical Transfer of Single–copy Eucaryotic Genes Using Total Cellular DNA as Donor", *Cell,* 14:725–731 (1978).

Abrams, "Optimal Strategies for Developing Human–Human Monoclonal Antibodies", *Meth. Enzym.,* 121:107–119 (1986).

Birnboim et al., "A rapid alkaline extraction procedure for screening recombinant plasmid DNA", *Nucleic Acids Research,* 7:1513–1523 (1979).

Bories et al., "A Fertile Pair", *Cell,* 59:955–958 (1989).

Boss, "An Improved in Vitro Immunization Procedure for the Production of Monoclonal Antibodies", *Meth. Enzym.,* 121:27–33 (1986).

Buck et al., "Monoclonal Antibodies Specific for Cell Culture Mycoplasmas", *In Vitro,* 18:377–381 (1982).

Campanelli et al., "Cloning of cDNA for Proteinase 3: A Serine Protease, Antibiotic, and Autoantigen from Human Neutrophils", *J. Exp. Med.,* 172:1709–1715 (1990).

Cohen, "Nonchromosomal Antibiotic Resistance in Bacteria: Genetic Transformation of *Escherichia coli* by R–Factor DNA", *PNAS(USA),* 69:2110–2114 (1972).

Crawford et al., "Production of Human Monoclonal Antibody to X31 Influenza Virus Nucleoprotein", *J. of General Virology,* 64:697–700 (1983).

Croce et al., "Production of human hybridomas secreting antibodies to measles virus", *Nature,* 288:488–489 (1980).

Decker et al., "Cell–Associated Tumor Necrosis Factor (TNF) as a Killing Mechanism of Activated Cytotoxic Macrophages", *J. of Immunol.,* 138:957–962 (1987).

Doherty et al., "Cephalosporin antibiotics can be modified to inhibit human leukocyte elastase", *Nature,* 332:192–194 (1986).

Duff et al., Tumor necrosis factor (TNF) and interleukin 1 (IL 1) in arthritis), *International Conference on Tumor Necrosis Factor and Related Cytotoxins,* 175:10 (1987).

Fendly et al., "Murine Monoclonal Antibodies Defining Neutralizing Epitopes on Tumor Necrosis Factor", *Hybridoma,* 6:359–370 (1987).

Graham et al., "A New Technique for the Assay of Infectivity of Human Adenovirus 5 DNA", *Virology,* 52:456–467 (1973).

Ish–Horowicz et al., "Rapid and efficient cosmid cloning", *Nucleic Acids Res.,* 9:2989–2998 (1981).

Knauf et al., "Relationship of Effective Molecular Size to Systemic Clearance in Rats of Recombinant Interleukin–2 Chemically Modified with Water–soluble Polymers", *J. Bio. Chem.,* 263:15064–15070 (1988).

Kohler et al., "Continuous cultures of fused cells secreting antibody of predefined specificity", *Nature,* 256:495 (1975).

Kozbor et al., "The production of monoclonal antibodies from human lymphocytes", *J. Immun. Today,* 4:72–79 (1983).

Kramer et al., "Oligonucleotide–Directed Construction of Mutations via Gapped Duplex DNA", *Meth. Enzym.,* 154:350–367 (1986).

Kriegler et al., "Transformation Mediated by the SV40 T Antigens: Separation of the Overlapping SV40 Early Genes with a Retroviral Vector", *Cell,* 38:483–491 (1984).

Larrick, "Plate Fusion Technique for Nonadherent Cells", *Human Hybridomas and Monoclonal Antibodies,* E.G. Engleman, S.K.H. Foung, J.W. Larrick and A.A. Raubitschek, Ed., Plenum Press, NY, p. 446, 448 (1985).

Luben et al., "In Vitro Immunization as an Adjunct to the Production of Hybridomas Producing Antibodies Against the Lymphokine Osteoclast Activating Factor", *Molecular Immunology,* 17:635–639 (1980).

Maki, "Nosocomial Bacteremia, An Epidemiologic Overview", *Nosocomial Infect.,* (Dikson, R.E., Ed), pp. 183–196, Yrke Medical Books, U.S.A. (1981).

Maniatis et al., *Molecular Cloning: A Laboratory Manual,* Cold Spring Harbor Press, pp. 254–255 (1984).

Matteucci et al., "Synthesis of Deoxyoligonucleotides on a Polymer Support", *J. Am. Chem. Soc.,* 103:3185–3191 (1981).

Kam et al, Feb. 1992. Substrate and inhibitor studies on proteinase 3. FEBS lett 297: 119–123.

Oleksyszyn et al, 1991. Irreverisble inhibition of serine proteases by peptide derivatives of (α–aminoalkyl)phosphonate diphenyl esters. Biochemistry 30: 485–493.

Bone, 1991. The pathogenesis of sepsis. Ann Int Med 115: 457–469.

Folks et al, 1989. Tumor necrosis factor α–0 induces expression of human immunodeficiency virus in chronically infected T–cell clone. Proc Natl Acad Sci USA 86: 2365–2368.

Kriegler et al (1988) A Novel Form of TNF/Cachectin In a Cell Surface Cytotoxic Transmembrane Protein. Cell. 53:45–53.

Kamijo et al (1989) Induction of Differentiation of Human Monoblastic and Myoblastic Leukemia Cell Lines by TNF Muteins. Biochem Biophys Res Comm. 160: 820–827.

Williams et al. (1994) Exp. Opin. Invest. Drugs. vol. 3(10):1051–1056.

Natanson et al. (1994) Annals of Internal Medicine vol. 120(9):771–783.

Lazar et al. (1988) Molecular & Cellular Biology. vol. 8(3):1247–1252.

Burgess et al. (1990) Journal of Cell Biology. vol. 111:2129–2138.

Tao et al. (1989) Journal of Immunology vol. 143(8):2595–2601.

Gillies et al. (1990) Hum. Antibod. Hybridomas vol. 1(1):47–54.

Solorzano et al. J. of Immunology, vol. 158:414–419, 1997. Vitro

-76

| | | | | | | | | | |
|---|---|---|---|---|---|---|---|---|---|
| ATG | AGC | ACT | GAA | AGC | ATG | ATC | CGG | GAC | GTG | GAG | CTG |
| Met | Ser | Thr | Glu | Ser | Met | Ile | Arg | Asp | Val | Glu | Leu |

```
ATG AGC ACT GAA AGC ATG ATC CGG GAC GTG GAG CTG
Met Ser Thr Glu Ser Met Ile Arg Asp Val Glu Leu

GCC GAG GAG GCG CTC CCC AAG AAG ACA GGG GGG CCC
Ala Glu Glu Ala Leu Pro Lys Lys Thr Gly Gly Pro

CAG GGC TCC AGG CGG TGC TTG TTC CTC AGC CTC TTC
Gln Gly Ser Arg Arg Cys Leu Phe Lue Ser Leu Phe

TCC TTC CTG ATC GTG GCA GGC GCC ACC ACG CTC TTC
Ser Phe Leu Ile Val Ala Gly Ala Thr Thr Leu Phe

TGC CTG CTG CAC TTT GGA GTG ATC GGC CCC CAG AGG
Cys Leu Leu His Phe Gly Val Ile Gly Pro Gln Arg

GAA GAG TCC CCC AGG GAC CTC TCT CTA ATC AGC CCT
Glu Glu Ser Pro Arg Asp Leu Ser Leu Ile Ser Pro

CTG GCC CAG GCA GTC AGA TCA TCT TCT CGA ACC CCG
Leu Ala Gln Ala Val Arg Ser Ser Ser Arg Thr Pro

AGT GAC AAG CCT GTA GCC CAT GTT GTA GCA AAC CCT
Ser Asp Lys Pro Val Ala His Val Val Ala Asn Pro

CAA GCT GAG GGG CAG CTC CAG TGG CTG AAC CGC CGG
Gln Ala Glu Gly Gln Leu Gln Trp Leu Asn Arg Arg

GCC AAT GCC CTC CTG GCC AAT GGC GTG GAG CTG AGA
Ala Asn Ala Leu Leu Ala Asn Gly Val Glu Leu Arg

GAT AAC CAG CTG GTG GTG CCA TCA GAG GGC CTG TAC
Asp Asn Gln Leu Val Val Pro Ser Glu Gly Leu Tyr

CTC ATC TAC TCC CAG GTC CTC TTC AAG GGC CAA GGC
Leu Ile Tyr Ser Gln Val Leu Phe Lys Gly Gln Gly

TGC CCC TCC ACC CAT GTG CTC CTC ACC CAC ACC ATC
Cys Pro Ser Thr His Val Leu Leu Thr His Thr Ile

AGC CGC ATC GCC GTC TCC TAC CAG ACC AAG GTC AAC
Ser Arg Ile Ala Val Ser Tyr Gln Thr Lys Val Asn

CTC CTC TCT GCC ATC AAG AGC CCC TGC CAG AGG GAG
Leu Leu Ser Ala Ile Lys Ser Pro Cys Gln Arg Glu

ACC CCA GAG GGG GCT GAG GCC AAG CCC TGG TAT GAG
Thr Pro Glu Gly Ala Glu Ala Lys Pro Trp Tyr Glu

CCC ATC TAT CTG GGA GGG GTC TTC CAG CTG GAG AAG
Pro Ile Tyr Leu Gly Gly Val Phe Gln Leu Glu Lys

GGT GAC CGA CTC AGC GCT GAG ATC AAT CGG CCC GAC
Gly Asp Arg Leu Ser Ala Glu Ile Asn Arg Pro Asp

TAT CTC GAC TTT GCC GAG TCT GGG CAG GTC TAC TTT
Tyr Leu Asp Phe Ala Glu Ser Gly Gln Val Tyr Phe
                        157
GGG ATC ATT GCC CTG
Gly Ile Ile Ala Leu
```

FIG. 1C

```
  1 / 1                                          31 / 11
ATG GCT CAC CGG CCC CCC AGC CCT GCC CTG    GCC TTG CTG CTG
MET ALA HIS ARG PRO PRO SER PRO ALA LEU    ALA LEU LEU LEU

61 / 21                                         91 / 31
AGC GGT GCT GCC CGA GCT GCG GAG ATC GTG    GGC TCC GTG CTG
SER GLY ALA ALA ARG ALA ALA GLU ILE VAL    GLY SER VAL LEU

121 / 41                                        151 / 51
TAC ATG GCC TCC CTG CAG ATG CGG GGG AAC    CCG GGC AGC CAC
TYR MET ALA SER LEU GLN MET ARG GLY ASN    PRO GLY SER HIS

181 / 61                                        211 / 71
GGC ACC TTG ATC CAC CCC AGC TTC GTG CTG    ACG GCC GCG CAC TGC CTG
GLY THR LEU ILE HIS PRO SER PHE VAL LEU    THR ALA ALA HIS CYS LEU

241 / 81                                        271 / 91
CCC CAG CGC CTG GTG AAC GTG GTG CTC GGA    GCC CAC AAC GTG CGG ACG CGG GAC ATA GAG CAG CCC
PRO GLN ARG LEU VAL ASN VAL VAL LEU GLY    ALA HIS ASN VAL ARG THR ARG ASP ILE GLU GLN PRO
```

FIG. 2 (1 of 3)

```
ACC CAG CAG CAC TTC  301/101  TCG GCT CAG GTG TTT CTG AAC AAC TAC  331/111  GAC GCG GAG AAC
THR GLN GLN HIS PHE           SER ALA GLN VAL PHE LEU ASN ASN TYR           ASP ALA GLU ASN

AAA CTG AAC GAC GTT CTC  361/121  CTC ATC CTG CAG CCA GCC AAC CTC  391/131  AGT GCC TCC
LYS LEU ASN ASP VAL LEU           LEU ILE LEU GLN PRO ALA ASN LEU           SER ALA SER

GTC GCC ACA GTC CAG CTG CCA  421/141  CAG CAG GAC CAG CCA GTG CCC CAC  451/     GGC ACC CAG TGC
VAL ALA THR VAL GLN LEU PRO           GLN GLN ASP GLN PRO VAL PRO HIS           GLY THR GLN CYS

151
CTG GCC ATG GGC TGG GGC CGC GTG  481/161  CAC GAC CCC CCA GCC CAG GTC CTG  511/     CAG
LEU ALA MET GLY TRP GLY ARG VAL           HIS ASP PRO PRO ALA GLN VAL LEU           GLN

171/
GAG CTC AAT GTC ACC GTG GTC ACC TTC  541/181  TGC CGG CCA CAT AAC ATT TGC ACT TTC
GLU LEU ASN VAL THR VAL VAL THR PHE           CYS ARG PRO HIS ASN ILE CYS THR PHE
```

FIG. 2 (2 OF 3)

```
571 /  191
GTC CCT CGC AAG GCC GGC ATC TGC TTC                601 /  201
VAL PRO ARG ARG LYS ALA GLY ILE CYS PHE            GGA GAC TCA GGT GGC CCC CTG ATC TGT
                                                   GLY ASP SER GLY GLY PRO LEU ILE CYS

631 /  211
GAT ATC ATC CAA GGA ATA GAC TCC TTC GTG            661 /  221
ASP ILE ILE GLN GLY ILE ASP SER PHE VAL            TGG ATC TGG GGA TGT GCC ACC CGC CTT
                                                   TRP ILE TRP GLY CYS ALA THR ARG LEU

691 /  231
TTC GAC TTC ACG CGG GTA GCC CTC TAC GTG            721 /  241
PHE ASP PHE THR ARG VAL ALA LEU TYR VAL            GAC TGG ATC CGT TCC ACG CTG
                                                   ASP TRP ILE ARG SER THR LEU

751 /  251
CGC CGT GTG GAG GCC AAG GGC CGC CCC TGA
ARG ARG VAL GLU ALA LYS GLY ARG PRO OPA
```

FIG. 2 (3 OF 3)

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 699 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 1..699

(ix) FEATURE:
      (A) NAME/KEY: mat_peptide
      (B) LOCATION: 229..699

(xi) SEQUENCE DESCRIPTION: SEQ ID NO:1:

```
ATG AGC ACT GAA AGC ATG ATC CGG GAC GTG GAG CTG GCC GAG GAG GCG       48
Met Ser Thr Glu Ser Met Ile Arg Asp Val Glu Leu Ala Glu Glu Ala
-76 -75              -70                 -65

CTC CCC AAG AAG ACA GGG GGC CCC CAG GGC TCC AGG CGG TGC TTG TTC       96
Leu Pro Lys Lys Thr Gly Gly Pro Gln Gly Ser Arg Arg Cys Leu Phe
-60             -55                 -50                 -45

CTC AGC CTC TTC TCC TTC CTG ATC GTG GCA GGC GCC ACC ACG CTC TTC      144
Leu Ser Leu Phe Ser Phe Leu Ile Val Ala Gly Ala Thr Thr Leu Phe
                -40                 -35                 -30

TGC CTG CTG CAC TTT GGA GTG ATC GGC CCC CAG AGG GAA GAG TCC CCC      192
Cys Leu Leu His Phe Gly Val Ile Gly Pro Gln Arg Glu Glu Ser Pro
            -25                 -20                 -15

AGG GAC CTC TCT CTA ATC AGC CCT CTG GCC CAG GCA GTC AGA TCA TCT      240
Arg Asp Leu Ser Leu Ile Ser Pro Leu Ala Gln Ala Val Arg Ser Ser
        -10                 -5                   1

TCT CGA ACC CCG AGT GAC AAG CCT GTA GCC CAT GTT GTA GCA AAC CCT      288
Ser Arg Thr Pro Ser Asp Lys Pro Val Ala His Val Val Ala Asn Pro
  5                 10                  15                  20

CAA GCT GAG GGG CAG CTC CAG TGG CTG AAC CGC CGG GCC AAT GCC CTC      336
Gln Ala Glu Gly Gln Leu Gln Trp Leu Asn Arg Arg Ala Asn Ala Leu
                25                  30                  35

CTG GCC AAT GGC GTG GAG CTG AGA GAT AAC CAG CTG GTG GTG CCA TCA      384
Leu Ala Asn Gly Val Glu Leu Arg Asp Asn Gln Leu Val Val Pro Ser
                40                  45                  50

GAG GGC CTG TAC CTC ATC TAC TCC CAG GTC CTC TTC AAG GGC CAA GGC      432
Glu Gly Leu Tyr Leu Ile Tyr Ser Gln Val Leu Phe Lys Gly Gln Gly
                55                  60                  65

TGC CCC TCC ACC CAT GTG CTC CTC ACC CAC ACC ATC AGC CGC ATC GCC      480
Cys Pro Ser Thr His Val Leu Leu Thr His Thr Ile Ser Arg Ile Ala
            70                  75                  80

GTC TCC TAC CAG ACC AAG GTC AAC CTC CTC TCT GCC ATC AAG AGC CCC      528
Val Ser Tyr Gln Thr Lys Val Asn Leu Leu Ser Ala Ile Lys Ser Pro
 85                  90                  95                 100

TGC CAG AGG GAG ACC CCA GAG GGG GCT GAG GCC AAG CCC TGG TAT GAG      576
Cys Gln Arg Glu Thr Pro Glu Gly Ala Glu Ala Lys Pro Trp Tyr Glu
                105                 110                 115

CCC ATC TAT CTG GGA GGG GTC TTC CAG CTG GAG AAG GGT GAC CGA CTC      624
Pro Ile Tyr Leu Gly Gly Val Phe Gln Leu Glu Lys Gly Asp Arg Leu
                120                 125                 130
```

```
AGC GCT GAG ATC AAT CGG CCC GAC TAT CTC GAC TTT GCC GAG TCT GGG      672
Ser Ala Glu Ile Asn Arg Pro Asp Tyr Leu Asp Phe Ala Glu Ser Gly
    135                 140                 145

CAG GTC TAC TTT GGG ATC ATT GCC CTG                                   699
Gln Val Tyr Phe Gly Ile Ile Ala Leu
    150                 155
```

(2) INFORMATION FOR SEQ ID NO:2:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Thr Glu Ser Met Ile Arg Asp Val Glu Leu Ala Glu Glu Ala
-76 -75             -70                 -65

Leu Pro Lys Lys Thr Gly Gly Pro Gln Gly Ser Arg Arg Cys Leu Phe
-60             -55                 -50                 -45

Leu Ser Leu Phe Ser Phe Leu Ile Val Ala Gly Ala Thr Thr Leu Phe
                -40                 -35                 -30

Cys Leu Leu His Phe Gly Val Ile Gly Pro Gln Arg Glu Glu Ser Pro
            -25                 -20                 -15

Arg Asp Leu Ser Leu Ile Ser Pro Leu Ala Gln Ala Val Arg Ser Ser
    -10                 -5                   1

Ser Arg Thr Pro Ser Asp Lys Pro Val Ala His Val Val Ala Asn Pro
  5                 10                  15                  20

Gln Ala Glu Gly Gln Leu Gln Trp Leu Asn Arg Arg Ala Asn Ala Leu
                25                  30                  35

Leu Ala Asn Gly Val Glu Leu Arg Asp Asn Gln Leu Val Val Pro Ser
                40                  45                  50

Glu Gly Leu Tyr Leu Ile Tyr Ser Gln Val Leu Phe Lys Gly Gln Gly
                55                  60                  65

Cys Pro Ser Thr His Val Leu Leu Thr His Thr Ile Ser Arg Ile Ala
 70                  75                  80

Val Ser Tyr Gln Thr Lys Val Asn Leu Leu Ser Ala Ile Lys Ser Pro
 85                  90                  95                 100

Cys Gln Arg Glu Thr Pro Glu Gly Ala Glu Ala Lys Pro Trp Tyr Glu
                105                 110                 115

Pro Ile Tyr Leu Gly Gly Val Phe Gln Leu Glu Lys Gly Asp Arg Leu
                120                 125                 130

Ser Ala Glu Ile Asn Arg Pro Asp Tyr Leu Asp Phe Ala Glu Ser Gly
    135                 140                 145

Gln Val Tyr Phe Gly Ile Ile Ala Leu
    150                 155
```

(2) INFORMATION FOR SEQ ID NO:3:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..768

(xi) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GCT | CAC | CGG | CCC | CCC | AGC | CCT | GCC | CTG | GCG | TCC | GTG | CTG | CTG | GCC | 48 |
| Met | Ala | His | Arg | Pro | Pro | Ser | Pro | Ala | Leu | Ala | Ser | Val | Leu | Leu | Ala | |
| 1 | | | | 5 | | | | | 10 | | | | | 15 | | |
| TTG | CTG | CTG | AGC | GGT | GCT | GCC | CGA | GCT | GCG | GAG | ATC | GTG | GGC | GGG | CAC | 96 |
| Leu | Leu | Leu | Ser | Gly | Ala | Ala | Arg | Ala | Ala | Glu | Ile | Val | Gly | Gly | His | |
| | | | 20 | | | | | 25 | | | | | 30 | | | |
| GAG | GCG | CAG | CCA | CAC | TCC | CGG | CCC | TAC | ATG | GCC | TCC | CTG | CAG | ATG | CGG | 144 |
| Glu | Ala | Gln | Pro | His | Ser | Arg | Pro | Tyr | Met | Ala | Ser | Leu | Gln | Met | Arg | |
| | | 35 | | | | | 40 | | | | | 45 | | | | |
| GGG | AAC | CCG | GGC | AGC | CAC | TTC | TGC | GGA | GGC | ACC | TTG | ATC | CAC | CCC | AGC | 192 |
| Gly | Asn | Pro | Gly | Ser | His | Phe | Cys | Gly | Gly | Thr | Leu | Ile | His | Pro | Ser | |
| | 50 | | | | | 55 | | | | | 60 | | | | | |
| TTC | GTG | CTG | ACG | GCC | GCG | CAC | TGC | CTG | CGG | GAC | ATA | CCC | CAG | CGC | CTG | 240 |
| Phe | Val | Leu | Thr | Ala | Ala | His | Cys | Leu | Arg | Asp | Ile | Pro | Gln | Arg | Leu | |
| 65 | | | | | 70 | | | | | 75 | | | | | 80 | |
| GTG | AAC | GTG | GTC | CTC | GGA | GCC | CAC | AAC | GTG | CGG | ACG | CAG | GAG | CCC | ACC | 288 |
| Val | Asn | Val | Val | Leu | Gly | Ala | His | Asn | Val | Arg | Thr | Gln | Glu | Pro | Thr | |
| | | | | 85 | | | | | 90 | | | | | 95 | | |
| CAG | CAG | CAC | TTC | TCG | GTG | GCT | CAG | GTG | TTT | CTG | AAC | AAC | TAC | GAC | GCG | 336 |
| Gln | Gln | His | Phe | Ser | Val | Ala | Gln | Val | Phe | Leu | Asn | Asn | Tyr | Asp | Ala | |
| | | | 100 | | | | | 105 | | | | | 110 | | | |
| GAG | AAC | AAA | CTG | AAC | GAC | GTT | CTC | CTC | ATC | CAG | CTG | AGC | AGC | CCA | GCC | 384 |
| Glu | Asn | Lys | Leu | Asn | Asp | Val | Leu | Leu | Ile | Gln | Leu | Ser | Ser | Pro | Ala | |
| | | 115 | | | | | 120 | | | | | 125 | | | | |
| AAC | CTC | AGT | GCC | TCC | GTC | GCC | ACA | GTC | CAG | CTG | CCA | CAG | CAG | GAC | CAG | 432 |
| Asn | Leu | Ser | Ala | Ser | Val | Ala | Thr | Val | Gln | Leu | Pro | Gln | Gln | Asp | Gln | |
| | 130 | | | | | 135 | | | | | 140 | | | | | |
| CCA | GTG | CCC | CAC | GGC | ACC | CAG | TGC | CTG | GCC | ATG | GGC | TGG | GGC | CGC | GTG | 480 |
| Pro | Val | Pro | His | Gly | Thr | Gln | Cys | Leu | Ala | Met | Gly | Trp | Gly | Arg | Val | |
| 145 | | | | | 150 | | | | | 155 | | | | | 160 | |
| GGT | GCC | CAC | GAC | CCC | CCA | GCC | CAG | GTC | CTG | CAG | GAG | CTC | AAT | GTC | ACC | 528 |
| Gly | Ala | His | Asp | Pro | Pro | Ala | Gln | Val | Leu | Gln | Glu | Leu | Asn | Val | Thr | |
| | | | | 165 | | | | | 170 | | | | | 175 | | |
| GTG | GTC | ACC | TTC | TTC | TGC | CGG | CCA | CAT | AAC | ATT | TGC | ACT | TTC | GTC | CCT | 576 |
| Val | Val | Thr | Phe | Phe | Cys | Arg | Pro | His | Asn | Ile | Cys | Thr | Phe | Val | Pro | |
| | | | 180 | | | | | 185 | | | | | 190 | | | |
| CGC | CGC | AAG | GCC | GGC | ATC | TGC | TTC | GGA | GAC | TCA | GGT | GGC | CCC | CTG | ATC | 624 |
| Arg | Arg | Lys | Ala | Gly | Ile | Cys | Phe | Gly | Asp | Ser | Gly | Gly | Pro | Leu | Ile | |
| | | 195 | | | | | 200 | | | | | 205 | | | | |
| TGT | GAT | GGC | ATC | ATC | CAA | GGA | ATA | GAC | TCC | TTC | GTG | ATC | TGG | GGA | TGT | 672 |
| Cys | Asp | Gly | Ile | Ile | Gln | Gly | Ile | Asp | Ser | Phe | Val | Ile | Trp | Gly | Cys | |
| | 210 | | | | | 215 | | | | | 220 | | | | | |
| GCC | ACC | CGC | CTT | TTC | CCT | GAC | TTC | TTC | ACG | CGG | GTA | GCC | CTC | TAC | GTG | 720 |
| Ala | Thr | Arg | Leu | Phe | Pro | Asp | Phe | Phe | Thr | Arg | Val | Ala | Leu | Tyr | Val | |
| 225 | | | | | 230 | | | | | 235 | | | | | 240 | |
| GAC | TGG | ATC | CGT | TCC | ACG | CTG | CGC | CGT | GTG | GAG | GCC | AAG | GGC | CGC | CCC | 768 |
| Asp | Trp | Ile | Arg | Ser | Thr | Leu | Arg | Arg | Val | Glu | Ala | Lys | Gly | Arg | Pro | |
| | | | | 245 | | | | | 250 | | | | | 255 | | |
| TGA | | | | | | | | | | | | | | | | 771 |

(2) INFORMATION FOR SEQ ID NO:4:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala His Arg Pro Pro Ser Pro Ala Leu Ala Ser Val Leu Leu Ala
 1               5                  10                  15

Leu Leu Leu Ser Gly Ala Ala Arg Ala Ala Glu Ile Val Gly Gly His
            20                  25                  30

Glu Ala Gln Pro His Ser Arg Pro Tyr Met Ala Ser Leu Gln Met Arg
             35                  40                  45

Gly Asn Pro Gly Ser His Phe Cys Gly Gly Thr Leu Ile His Pro Ser
     50                  55                  60

Phe Val Leu Thr Ala Ala His Cys Leu Arg Asp Ile Pro Gln Arg Leu
 65                  70                  75                  80

Val Asn Val Val Leu Gly Ala His Asn Val Arg Thr Gln Glu Pro Thr
                 85                  90                  95

Gln Gln His Phe Ser Val Ala Gln Val Phe Leu Asn Asn Tyr Asp Ala
             100                 105                 110

Glu Asn Lys Leu Asn Asp Val Leu Leu Ile Gln Leu Ser Ser Pro Ala
        115                 120                 125

Asn Leu Ser Ala Ser Val Ala Thr Val Gln Leu Pro Gln Gln Asp Gln
    130                 135                 140

Pro Val Pro His Gly Thr Gln Cys Leu Ala Met Gly Trp Gly Arg Val
145                 150                 155                 160

Gly Ala His Asp Pro Pro Ala Gln Val Leu Gln Glu Leu Asn Val Thr
                165                 170                 175

Val Val Thr Phe Phe Cys Arg Pro His Asn Ile Cys Thr Phe Val Pro
            180                 185                 190

Arg Arg Lys Ala Gly Ile Cys Phe Gly Asp Ser Gly Gly Pro Leu Ile
        195                 200                 205

Cys Asp Gly Ile Ile Gln Gly Ile Asp Ser Phe Val Ile Trp Gly Cys
210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                245                 250                 255

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Protein
         (B) LOCATION: -2..14

(xi) SEQUENCE DESCRIPTION: SEQ ID NO:5:

Gln Ala Val Arg Ser Ser Ser Arg Thr Pro Ser Asp Lys Pro Val Ala
 -2      1               5                  10

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:
```

GTTTGCTACA ACATGGAGGT CCCTGGGGGA                                    30

(2) INFORMATION FOR SEQ ID NO:7:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION: -5..18

(xi) SEQUENCE DESCRIPTION: SEQ ID NO:7:

Pro Leu Ala Gln Ala Val Arg Ser Ser Ser Arg Thr Pro Ser Asp Lys
-5              1               5                   10

Pro Val Ala His Val Val Ala
            15

(2) INFORMATION FOR SEQ ID NO:8:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Arg Thr Pro Ser Asp Lys Pro Val Ala His Val Val Ala
1               5                   10

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION: -5..8

(xi) SEQUENCE DESCRIPTION: SEQ ID NO:9:

Pro Leu Ala Gln Ala Val Arg Ser Ser Ser Arg Thr Pro
-5              1               5

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION: -2..4

(xi) SEQUENCE DESCRIPTION: SEQ ID NO:10:

```
Gln Ala Val Arg Ser Ser
 -2           1

(2) INFORMATION FOR SEQ ID NO:11:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:11:

Val Arg Ser Ser
 1

(2) INFORMATION FOR SEQ ID NO:12:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: misc_feature
         (D) OTHER INFORMATION:
              /note= "The Xaa at position 1 is
              Boc."

(ix) FEATURE:
         (A) NAME/KEY: misc_feature
         (D) OTHER INFORMATION:
              /note= "The Xaa at position 6 is
              p(OPh)2."

(xi) SEQUENCE DESCRIPTION: SEQ ID NO:12:

Xaa Leu Ala Gln Ala Xaa
 1               5

(2) INFORMATION FOR SEQ ID NO:13:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Protein
         (B) LOCATION: -4..5

(xi) SEQUENCE DESCRIPTION: SEQ ID NO:13:

Leu Ala Gln Ala Val Arg Ser Ser Ser
 -4              1               5

(2) INFORMATION FOR SEQ ID NO:14:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Protein
```

-continued (B) LOCATION: -4..5

(xi) SEQUENCE DESCRIPTION: SEQ ID NO:14:

```
Gln Ala Val Arg Ser Ser Ser
 -2      1               5
```

COMPOSITIONS FOR THE INHIBITION OF TNF HORMONE FORMATION AND USES THEREOF

This is a continuation of U.S. application Ser. No. 07/905,546, filed Jun. 25, 1992, now abandoned, which is a continuation-in-part of U.S. application Ser. No. 07/395,253, filed Aug. 16, 1989, now abandoned.

FIELD OF THE INVENTION

This invention is in the area of immunology/biochemistry, and particularly concerns the development of compositions and methods for identifying inhibitors of protein hormone release, and prophylactic and therapeutic uses of the inhibitors for treating diseases associated with elevated levels of the hormones. More specifically, the invention facilitates the identification of compositions and methods for identifying inhibitors of a TNF convertase. These inhibitors may be used to treat a variety of diseases, particularly sepsis, rheumatoid arthritis, cachexia, AIDS and autoimmune diseases, and thus affords the physician alternate treatment regimes.

BACKGROUND OF THE INVENTION

In the United States alone nosocomial bacteremia develops in about 194,000 patients per year, and of these about 75,000 die. Maki, D. G., 1981, *Nosocomial Infect.,* (Dikson, R. E., Ed.), page 183, Yrke Medical Books, U.S.A. Most of these deaths are attributable to six major gram-negative bacilli—*Pseudomonas aeruginosa, Escherichia coli,* Proteus, Klebsiella, Enterobacter and Serratia. The current treatment for bacteremia is the administration of antibiotics which, have limited effectiveness in treatment of septic shock.

The precise pathology of bacteremia is not completely elucidated. Nevertheless, it is known that certain bacterial endotoxins called lipopolysaccharides (LPS), are the primary causative agent. LPS consists of at least three significant antigenic regions: lipid A; core polysaccharide; and O-specific polysaccharide. The latter is also referred to as O-specific chain or simply O-antigen. The O-specific chain region is a long-chain polysaccharide built up from repeating polysaccharide units. The number of polysaccharide units differs among different bacterial species and may vary from one to as many as six or seven monosaccharide units. While the O-specific chain varies among different gram-negative bacteria, the lipid A and core polysaccharides are similar if not identical.

Since LPS plays a key role in sepsis, many approaches have been pursued to neutralize its activity. Presently, there is considerable work which suggest that anti- LPS antibody will soon be a valuable clinical adjunct to the standard antibiotic therapy.

LPS initiates a cascade of biochemical events that eventually causes the death of the patient. It is widely believed that an early result of LPS introduction is the stimulation of macrophage cells and the production of tumor necrosis factor (TNF) as a result of LPS. Thus, considerable effort has been expended to produce neutralizing antibody to TNF, or other molecules that could inhibit its effects. It is likely that antibody to TNF will have valuable clinical applications. Tracey, et al., 1987, *Nature,* 330:662.

TNF has been shown to exist in both membrane-bound and soluble secreted forms. Decker, et al., 1987, *J. of Immunol.,* 138:957; Kriegler, et al., 1988, *Cell,* 53:45. Human TNF has been cloned and shown to consist of a 17 kD polypeptide, plus an unusually long 76 amino acid putative signal leader sequence. The 17 kD molecule is a key agent involved in initiating the biochemical cascade responsible for sepsis. It has been proposed by Kriegler, et al., 1988, *Cell,* 53:45, that TNF may exist as both a membrane bound 26 kD form, and a soluble form corresponding to the 17 kD species. The 26 kD form is the precursor, or prohormone, of the mature 17 kD molecule. It has further been proposed by Kriegler, et al. above, that the two forms of TNF may have different biological effects, primarily as a result of differences in tissue distribution.

It will be appreciated that because TNF plays a key role in causing sepsis and other diseases that there is a need to identify and develop anti-TNF prophylactics/therapeutics. As mentioned above, anti-TNF antibody appears to be promising, and has been shown to be effective in baboons. However, these studies have involved the use of non-human TNF and non-human TNF antibody. From a practical standpoint non-human anti-TNF antibody will have limited therapeutic application because of immunologic rejection of the antibody by a patient's immune system. Consequently, a human antibody, or a genetically engineered antibody consisting of the human constant region and the mouse variable region ("humanized antibody") is preferred.

TNF, in addition to playing a critical role in sepsis, has recently been shown to be involved in initiating the expression of human immunodeficiency virus in human cells that carry latent virus. Folks et al., 1989, *PNAS (USA),* 86:2365. Thus, preventing or inhibiting the formation of the 17 kD, or lower molecular weight forms of TNF might be a valuable prophylactic for the treatment of AIDS patients by preventing the expression of virus that is latent in the patient.

TNF also plays a role in various autoimmune diseases, particularly rheumatoid arthritis. Duff, et al., 1987, *International Conference on Tumor Necrosis Factor and Related Cytotoxins,* 175:10. Thus, compounds or methods for inhibiting TNF action will have considerable application for the treatment of a variety of diseases of immunologic origin.

In addition to antibody, other molecules with TNF inhibitory activity are being sought. Non-antibody TNF inhibitors are described by Seckinger, et al., 1988, *J. Exp. Med.,* 167:151, and Seckinger, et al, 1989, J. Biol. Chem,. 264:11966, and in European Patent Application No. 88830365.8, inventors Wallach, et al. The inhibitors are present in the urine of febrile patients, and have been purified and shown to have molecular weights of about 27,000–33,000. These inhibitors are now known to be soluble forms of the TNF receptor. Although these molecules exhibit TNF-inhibitory activity, neither of the inhibitors has yet been shown to be effective in the treatment of sepsis in humans.

From the foregoing discussion it is apparent that there is a need to identify and develop additional anti-TNF inhibitors, both antibody based or otherwise, that are efficacious in the treatment of sepsis.

SUMMARY OF THE INVENTION

In its most general form, the invention described herein presents methods and compositions for inhibiting the production of a mature form of TNF, from its prohormone precursor, proTNF. These compositions are useful for preventing or treating diseases in patients associated with elevated circulating levels of mature TNF. The invention also relates to a method for identifying molecules that inhibit the production of a mature form of TNF. Such inhibitors are distinguishable from anti- TNF antibody, which neutralizes TNF. This method can be used to identify medicaments such as prophylactics and/or therapeutics for the treatment of sepsis and other diseases caused by the production of mature TNF. These medicaments are able to interfere with the cleavage of the 26 kD proTNF prohormone by enzymes termed convertases. Thus, these medicaments inhibit the production of lower molecular weight sepsis-inducing molecules (i.e., 17 kD TNF). Specifically, the preferred inhibitors as described herein interfere with the activity of a TNF convertase to prevent removal of the N-terminal portion of the 26 kD molecule including at least the 76-amino-acid signal sequence to produce a mature form of TNF such as the 17 kD TNF. The invention also includes a class of compounds that are both inhibitors of a TNF convertase and effective in the prevention and/or treatment of sepsis. Compounds in this class include anti-convertase antibody, muteins of the prohormone form, and proteins or peptides that compete with the 26 kD form of TNF for binding to the convertase. Also claimed are small molecular weight compounds that specifically inhibit the class of proteases that includes TNF convertases, or preferably, show selective specificity for inhibition of TNF convertase.

Additionally, the present inventors have purified a TNF convertase to near-homogeneity, discovered its amino acid sequence, and compared it to known serine proteases. The purified TNF convertase contains an N-terminal amino acid sequence essentially identical to PR-3, a known neutrophil protease having the same molecular weight. They have also identified various inhibitors of TNF convertase and have tested them in in vitro and in vivo assays.

Specifically, an object of the present invention is to provide small molecules that specifically inhibit TNF convertases.

Another object of the invention is a method for treating diseases such as septicemia, septic shock, cerebral malaria, rheumatoid arthritis, AIDS, cachexia, and graft-versus-host disease by administering a PR-3 inhibitor.

In one aspect of this invention, a method for identifying a prophylactic or therapeutic of a disease caused by a mature tumor necrosis factor (TNF) produced from a proTNF by cleavage of said proTNF by a TNF convertase is provided, the method comprising the steps of:(a) contacting the proTNF with an amount of the TNF convertase effective for cleaving the proTNF; (b) measuring the conversion of the proTNF to the mature TNF in step (a); (c) repeating steps (a) and (b) further including a molecule sought to be identified as a prophylactic or therapeutic of diseases caused by the mature TNF; (d) measuring the conversion of the proTNF to the mature TNF in step (c); and (e) comparing the conversion measured in step (b) with the conversion measured in step (c) to determine whether the molecule is a suitable prophylactic or therapeutic of diseases caused by mature TNF.

In another aspect of the invention, a therapeutic or prophylactic compound for treating a disease caused by a mature TNF produced from a proTNF by cleavage of said proTNF by a TNF convertase is provided, the therapeutic or prophylactic identified by a method comprising the steps of: (a) contacting the proTNF with an amount of the TNF convertase effective for cleaving the proTNF; (b) measuring the conversion of the proTNF to the mature TNF in step (a); (c) repeating steps (a) and (b) further including a molecule sought to be identified as a prophylactic or therapeutic of diseases caused by the mature TNF; (d) measuring the conversion of the proTNF to the mature TNF in step (c); and (e) comparing the conversion measured in step (b) with the conversion measured in step (c) to identify whether the molecule is a suitable prophylactic or therapeutic of diseases caused by mature TNF.

In yet another aspect of the invention, a method for treating a patient having a disease or susceptible to a disease caused by a mature TNF produced from a proTNF by cleavage of said proTNF by a TNF convertase is provided, the method comprising administering to a patient in need of such treatment an effective amount of an inhibitor of a TNF convertase. In a preferred embodiment, the disease is selected from the group consisting of sepsis, rheumatoid arthritis, cachexia, cerebral malaria, AIDS, and graft-versus-host disease.

In a further aspect of this invention, a pharmaceutical composition for the treatment of a disease caused by a mature TNF produced from a proTNF by cleavage of said proTNF by a TNF convertase is provided, the composition comprising an effective amount of an inhibitor of a TNF-convertase and a pharmaceutically acceptable excipient.

BRIEF DESCRIPTION OF THE DRAWINGS

FIG. 1C shows the DNA and amino acid sequences (SEQ ID NOS: 1 and 2 respectively) of the molecule.

FIG. 2 shows the predicted amino acid sequence (SEQ ID NO:4) of the unprocessed precursor of human PR-3, derived from the DNA sequence (SEQ ID NO:3) of the cDNA clone.

DETAILED DESCRIPTION OF THE INVENTION

Definitions

To facilitate understanding the nature and scope of applicant's invention, several definitions regarding various aspects of the invention are presented below. It will be understood, however, that these definitions are general in nature, and encompassed within the definitions are meanings well known to those skilled in the art. "Sepsis" is herein defined to mean a disease resulting from gram positive or gram negative bacterial infection, the latter primarily due to the bacterial endotoxin, lipopolysaccharide (LPS). It can be induced by at least the six major gram-negative bacilli and these are *Pseudomonas aeruginosa, Escherichia coli,* Proteus, Klebsiella, Enterobacter and Serratia.

The terms "prohormone" and "mature" hormone have the following meanings. "Prohormone" is intended to cover proteins that contain a peptide segment which is removed during the in vivo production of the "mature" form of the hormone. Preferably, these are proteins produced at least in part by cells of the immune system, such as T-cells or macrophages. The preferred embodiment of the invention is the 26 kD proTNF prohormone, or "proTNF" as discussed in detail below. ProTNF SEQ ID NO:2 is cleaved primarily to a 17 kD mature form i.e., amino acid residues 1-157 of SEQ ID NO:2, preferably having the N-terminal sequence of "mature TNF", Val-Arg-Ser-Ser (SEQ ID NO:11). However, "mature TNF" is intended to include other cleavage products also formed from the prohormone. These cleavage products will retain the biological characteristics of the 17 kD form of mature TNF, and are truncated (i.e., cleaved) forms of proTNF wherein at least the N-terminal 76-amino acid leader sequence (SEQ ID NO:2 is removed.

Figure 1A:
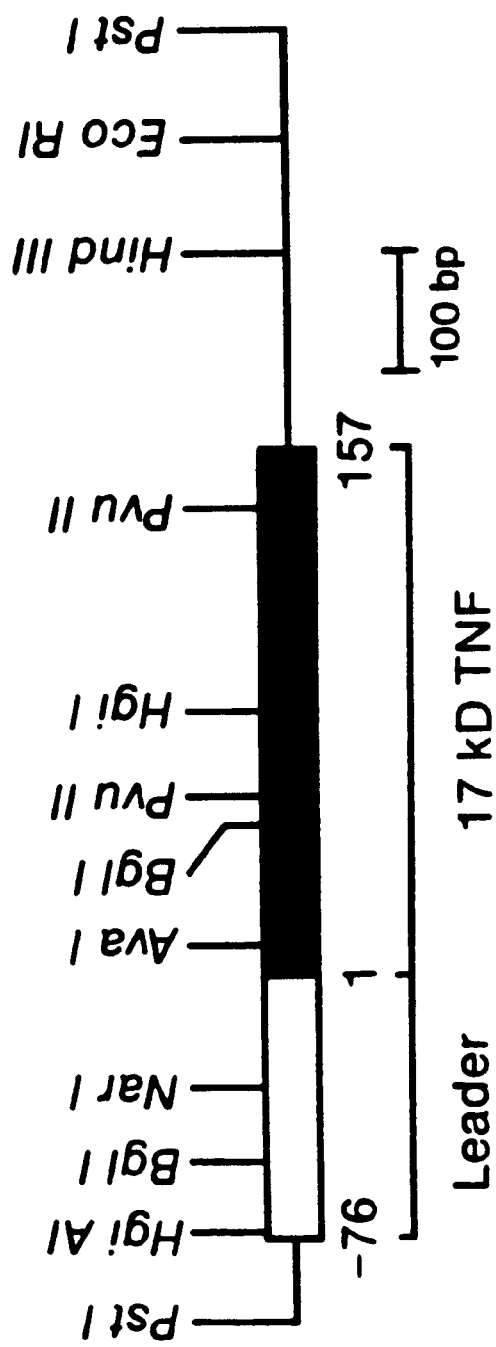
FIG. 1A shows the restriction map of the DNA sequence that encodes 26 kD proTNF.
Figure 1B:
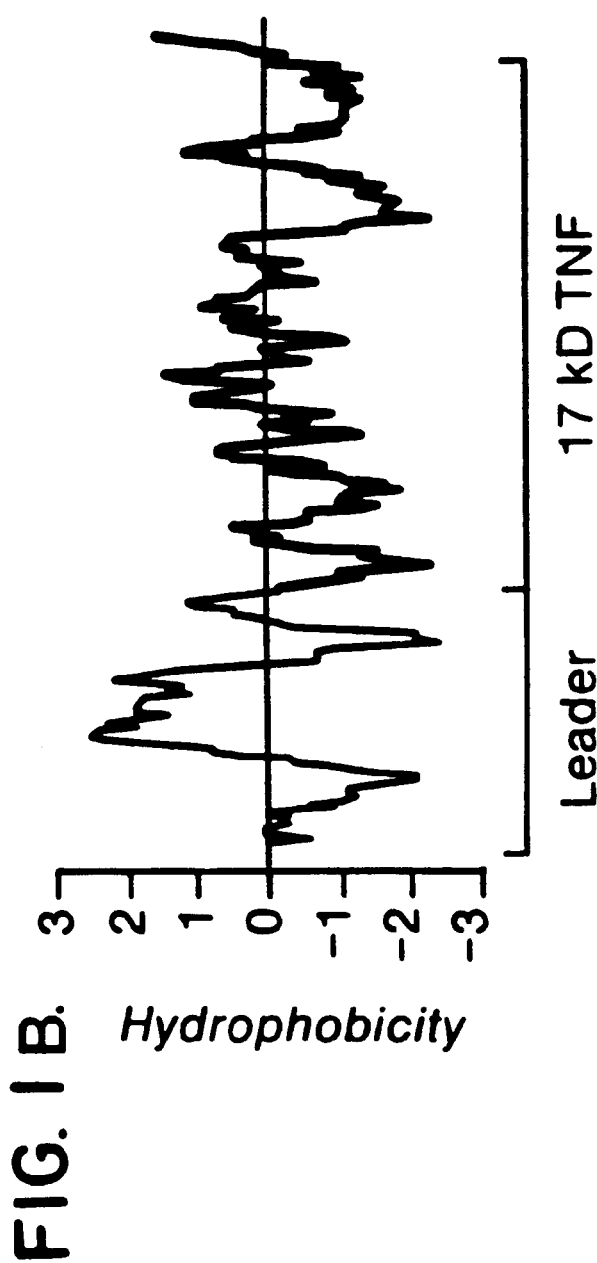
FIG. 1B shows a hydrophobicity plot of 26 kD proTNF.

As used herein, "proTNF" refers to TNF having a molecular weight of about 26,000, which is the prohormone form of TNF-α (reference cloned sequence of FIG. 1). It is known that the propeptide segment of a prohormone varies in length depending on the species from which it is derived, but the amino acid sequence of this segment is highly conserved. Indeed, in the mouse, approximately 86% of the 79-amino acids that make up the putative leader sequence of the prohormone are identical to the 76 known amino acids that comprise the putative leader of human TNF. Thus, it will be appreciated by those skilled in the art that when reference is made to proTNF it is intended that the molecule can be derived from any particular species so that it may have a slightly altered leader sequence compared to the human sequence as is known in the art.

The term "convertase" or "TNF convertase", as used herein, refers to one or more enzymes normally present in an animal that are capable of cleaving 26 kD proTNF to a mature TNF having TNF biological activity in trimeric form in a TNF bioassay. In unstimulated cells, a convertase is recovered largely in fractions consisting substantially of membranes, although some activity is located in the cytosol. A TNF convertase is normally associated with cells that produce TNF. One TNF convertase SEQ ID NO:4 is now known to be the serine protease "proteinase-3", also called "PR-3", "P-29B" or "myeloblastin".

The phrase "membrane-associated" as applied to TNF convertase indicates a form of the convertase that is initially isolated in substantially insoluble form, as indicated by the presence of much of the convertase activity in a 30,000×g pellet fraction. However, some TNF convertase is soluble when isolated from neutrophil granules.

"Recombinant antibody" refers to antibody wherein one portion of each of the amino acid sequences of heavy and light chain is homologous to corresponding sequences in antibody derived from a particular species or belonging to a particular class, while the remaining segment of the chains is homologous to corresponding sequences in another. Most commonly, in a recombinant antibody the variable region of both light and heavy chain copies the variable regions of antibody derived from one species of mammal, while the constant regions are homologous to the sequences in antibody derived from another. One example is "humanized" mouse antibody where the constant regions of the mouse antibody are replaced with a human constant region.

In its most general form, the instant invention concerns methods and compositions for identifying inhibitors of diseases associated with the production of mature hormones from their prohormone forms. The preferred embodiment of a prohormone is 26 kD proTNF (SEQ ID NO:2), which is then cleaved to a lower molecular weight "mature" form, preferably 17 kD (amino acid residues 1 to 157 of SEQ ID NO:2), which, in its multimeric (usually trimeric) form, is substantially involved in producing life-threatening physiological changes associated with sepsis. Thus, molecules which are capable of interfering with the conversion of the 26 kD proTNF to the mature form are useful for preventing or treating sepsis.

The assays described herein detect the conversion of a prohormone to its mature hormone form, with the preferred embodiment being the enzymatic conversion of the 26 kD molecular weight form of TNF to, preferably, a 17,000 molecular weight form. The enzyme responsible for the conversion is termed "TNF convertase". Thus, the invention is most readily presented in four parts. Part one shows the materials and methods for realizing proTNF, the 26 kD form of TNF. Part two identifies sources of TNF-convertase, and methods for purifying the enzyme. Part three describes the identification of various convertase inhibitors. Finally, part four of the invention presents a description of ways of using the inhibitors to treat patients suffering from sepsis or other diseases. Each of these sections will now be addressed separately.

Several patents/patent applications and scientific references are referred to below. The instant invention draws on some of the material and methods shown in these references, and thus it is intended that all of the references, in their entirety, be incorporated by reference.

I. 26 kD proTNF

The TNF and proTNF of the current invention may be obtained in native, synthetic or recombinant forms by methods known in the art. While the recombinant systems described below render the 26 kD proTNF obtainable in considerable amounts and facilitate the assay procedures for TNF inhibitors, it will be appreciated that non-recombinant systems may also be used. For instance, it has been shown that the 26 kD molecule can be identified in stimulated monocytes. Kriegler, et al., 1988, *Cell,* 53:45. Thus, a suitable assay procedure is to stimulate monocytes to produce the 26 kD proTNF molecule, and then to measure the disappearance of the 26 kD molecule as a result of action by the convertase. Preferably the 17,000 molecular weight mature TNF is generated.

The 26 kD proTNF (SEQ ID NO:2) is cleaved by convertase at one or more internal sites to generate "mature TNF". The major site is at the junction which separates the secreted form of TNF (the 17 kD species) from the leader sequence. The sequence at this junction is Gln-Ala-Val-Arg-Ser-Ser- (SEQ ID NO:10). The major cleavage site lies between alanine and valine, since valine is known to be the amino-terminal amino acid of the 17 kD molecule (the primary mature form). Several other species of TNF may be produced by the convertase, and these are the products of minor or secondary cleavage sites: for example, between the Val and the Arg in the sequence above, or between Pro and the Val located at +12 and +13 in the amino acid sequence. The assays described herein can monitor the inhibition of the conversion of the 26 kD proTNF species, or the appearance of a mature TNF form irrespective of its cleavage site.

The proTNF form and mature TNF form have been cloned and expressed in a number of systems. For instance, the cloning of rabbit TNF is disclosed in EP 146,026, published Jun. 26, 1985 (Dainippon Pharmaceutical Co., Ltd.) and EP 148,311, published Jul. 17, 1985 (Asahi Kasei Kogyo Kabushiki). The cloning of human TNF having 151 and 155 amino acids (2 and 6 less than the native mature form) is disclosed in EP 155,549, published Sep. 25, 1985 (Dainippon Pharmaceutical Co., Ltd.), and human TNF having 155 amino acids is disclosed in EP 158,286, published Oct. 16, 1985 (Asahi Kasei Kogyo Kabushiki Kaisha) and corresponding GB 1,158,829A, published Nov. 20, 1985. The cloning of mature TNF (157 amino acids) and various modified forms (muteins) thereof is disclosed in EP 168,214, published Jan. 15, 1986 (Genentech) and PCT US 85/01921, filed Oct. 3, 1985, (Cetus Corporation).

In addition, U.S. Pat. Nos. 4,677,063 and 4,677,064 show cDNA sequences that encode the 26,000 and 17,000 forms of TNF, as well as muteins of these molecules.

The cDNA sequence (SEQ ID NO:1) that encodes the 26 kD proTNF species (SEQ ID NO:2) is preferably obtained from the plasmid, pB 11, described in commonly owned co-pending application, U.S. Ser. No. 670,360, filed Nov. 9, 1984; and U.S. Pat. Nos. 4,677,063 and 4,677,064. The plasmid pB 11 contains the SV40 promoter in operable linkage to the proTNF coding sequence, and thus is useful for expressing the 26 ID TNF species in eukaryotic host cells. Additionally, a second plasmid which contains the entire sequence which encodes the 26 kD proTNF species is described in the forgoing U.S. patent application and patents. It is designated pE4. The plasmid pE4 is on deposit with the American Type Culture Collection, Accession No. 39894.

The cDNA sequence (SEQ ID NO:1) that encodes the 26 kD proTNF species (SEQ ID NO:2) is present in the plasmid pB 11 as a PstI fragment. Thus, it is readily removed and inserted into any one of a number of suitable expression systems. The preferred expression system is the plasmid pFVXM, which is described in co-pending U.S. Ser. No. 855,865, entitled Infective Drug Delivery System, inventor Kriegler, et al. (abandoned in favor of U.S. Ser. No. 571,017, filed Aug. 22, 1990). PFVXM is on deposit with the American Type Culture Collection and has Accession No. 67,103.

pFVXM is a retroviral vector that was derived from the plasmid pEVX described by Kriegler, et al., 1984, in *Cell,* 38:483. pEVX has a Moloney murine leukemia virus derived splice donor site 3' to the 5'—long terminal repeat. It was previously shown that this splice donor sequence decreases the yield of correctly spliced translational templates of retroviral constructions. Thus, pEVX was engineered to remove the splice donor site, and replaced with an analogous SmaI fragment of the Harvey murine sarcoma virus genome, which lacks the Moloney murine leukemia virus splice donor sequence. The resulting vector, pFVXM, lacks the Moloney murine leukemia virus spliced donor sequence and carries a viral packaging sequence. pFVXM has a convenient PstI site in which the DNA sequences that encodes the 26 kD proTNF species can be inserted.

II. TNF Convertase

TNF convertase activity arises from the proteolytic action of one or more enzymes. A variety of biological materials are available as sources of TNF convertase activity. These include tissues, cells, or extracts, or fluids associated therewith that are preferably, but not necessarily, of immunologic origin. Moreover, established cell lines may also be utilized. Suitable sources would include human peripheral blood mononuclear cells, such as leukocytes or cell lines of leukocyte origin, preferably macrophages and monocytes. Neutrophils are a particularly useful source of TNF- convertase. Because of the ease of manipulating established cell lines, one preferred cell source of TNF convertase is HL60. Thus, the conversion of the 26 kD proTNF species to mature TNF can be affected by combining the 26 kD species with either intact HL60 cells, extracts derived therefrom, or media in which the HL60 cells were grown and thus contains TNF convertase activity. In some cell types, TNF convertase activity is present in the culture medium after the appropriate stimulation, which is discussed more below. Further, because the TNF convertase activity is partially membrane-associated under certain conditions, it is possible to obtain a membrane fraction that may be utilized.

The procedures for isolating monocytes are well known in the art, as are other methods for culturing cell lines such as HL60. Briefly, monocytes may be prepared from peripheral blood by centrifugation first through Ficoll-hypaque and Percoll (49.2%) using standard procedures. This yields an enriched population of monocytes and lymphocytes, and the monocytes can be further enriched by plating the mixture of cells onto tissue culture dishes and incubating the cells for a time sufficient to permit the monocytes to adhere to the surface of the dishes. The lymphocytes are then washed off of the plates leaving primarily adherent monocytes. These cells may then be used as is, or can be stimulated to produce enhanced levels of TNF convertase using known monocyte activators, preferably lipopolysaccharide and phorbol myristate acetate. The cells may be fractionated, and either an extract or a membrane fraction prepared therefrom and employed in the assays described below.

We have isolated TNF convertase from 12 liters of HL60 culture by isolating the cell membrane fraction, solubilizing it in a 0.5% Nonidet P-40 detergent, subjecting the solution to anion exchange chromatography, cation exchange-HPLC, anion exchange-HPLC, and reverse-phase HPLC to yield 20 $\mu$g of 1,000-fold purified TNF convertase, which is equivalent to ~320 Units at an 18% yield. The convertase was found to have a molecular weight of approximately 29–30 kD by SDS-PAGE analysis (silver-stained). The convertase was sequenced, and the first amino acids were found to be identical, within experimental error, to the mature N-terminal sequence of a known neutrophil proteinase, PR-3 (Campanelli et al., 1990, *J. Exp. Med.,* 172:1709–1715). The purified convertase was shown to cleave the 26 kD proTNF to the 17 kD mature form.

As described more fully below, the amino acid sequence for PR-3 (SEQ ID NO:4) has been elucidated, as predicted from the sequence of the cDNA clone (SEQ ID NO:3) shown in FIG. 2. PR-3 is known in the art as a protease having activities unrelated to TNF processing. It is classified as a human polymorphonuclear leukocyte serine proteinase that degrades elastin, fibronectin, laminin, vitronectin, and collagen type IV; see Rao et al., 1991, *J. Biol. Chem..* 266:9540–9548. By SDS-PAGE analysis purified PR-3 has been reported to have a major band at 26.8 kD with two smaller bands having slightly larger molecular masses, possibly representing different glycosylated species, see Rao et al., supra. PR-3 is structurally similar to other serine proteases, such as elastase, cathepsin G, mouse granzyme B, rat mast cell protease II, human lymphocyte protease, and chymotrypsin; see Campanelli et al., 1990, *J. Exp. Med.,* 172:1709–1715. PR-3 is inhibited by (X2-macroglobulin, phenylmethyl-sulfonyl fluoride (PMSF), and $\alpha_1$-antitrypsin. Sequencing of the PR-3 digestion products of radiolabelled 26 kD proTNF show that PR-3 prefers to cleave the proTNF SEQ ID NO:2 to produce an N-terminal Val-Arg-Ser sequence (amino acids 1–3 of the 17 kD mature form) although cleavage may occur to produce an N-terminal Arg-Ser-Ser (amino acids 2-4) or Val-Ala-His (amino acids 13–15) sequences. Rao et al., supra, reports that PR-3 prefers small aliphatic amino acids in the substrate cleavage site. Serine proteases such as elastase, cathepsin G, and plasmin do not efficiently convert the 26 kD proTNF to the 17 kD mature form.

PR-3 may also be isolated from neutrophils. Neutrophils are separated from human blood, then granules and membranes are isolated, and the mixture is fractionated on RP-HPLC, as described below.

As shown below, PR-3 is inhibited by peptide diphenyl phosphonate inhibitors, elastinal, and dichloro-isocumarin (DCI). The peptide diphenyl phosphonate inhibitors include Boc-Val-PrVal-p(OPh)$_2$ and Boc-Ala-Pro-Val-p(OPh)$_2$. Boc-Ala-Gln-Ala-p(OPh)$_2$ and Boc-Leu-Ala-Gln-Ala-p(OPh)$_2$, (SEQ ID NO:12) have also been tested and have much less inhibitory activity. "Boc" means tert-butyloxycarbonyl and "p(OPh)$_2$" represents the diphenyl phosphonate moiety, wherein the formula -COOH group is replaced with —P(=O)(O-phenyl)$_2$. See Oleksyszyn et al., 1991, *Biochem.*, 30:485. It will be appreciated that other peptide diphenyl phosphonate molecules may inhibit PR-3. Potential inhibitors may be constructed using the procedures shown in Oleksyszyn et al., supra, using small aliphatic peptides, for an example. Once the potential inhibitors are made, they may be tested in the assays shown below. Modeling studies predict that Boc-Val-Pro-His-p(OPh)$_2$ will be a potent PR-3 inhibitor.

III. Inhibitors of TNF convertase Activity-Prophylactics or Therapeutics of Sepsis Inhibitors of convertase activity will also be prophylactics or therapeutics that may be used in the treatment of sepsis and certain other diseases in which circulating TNF has been implicated, including rheumatoid arthritis and cachexia Inhibitors of TNF convertase can be identified by procedures that enable one to measure the conversion of proTNF to mature TNF. Several such assay procedures are described herein, and in Example 4 below. A suitable assay would consist of combining 26 kD proTNF, a TNF convertase, and a putative inhibitor. It will be understood by those skilled in the art that the inhibitory material may be added to the convertase before the convertase is added to TNF, or it can be added to TNF prior to, or immediately after adding the convertase. The order of addition may facilitate identification of inhibitors, but it is not determinative. If a substance has inhibitory activity, this can be revealed by electrophoretic analysis of the solution which will reveal, relative to control reaction, an increase in the amount of the 26 kD species, and concomitantly a decrease in mature TNF species. Applicants have also identified a calorimetric assay to detect convertase inhibitors. The assay is convenient and correlates with the autoradiographic assay for cleavage of 26 kD proTNF (SEQ ID NO:2). The colorimetic assay is described in detail in Example 4. Also see Kam et al., 1992, *FEBS,* 297(1,2):119–123.

Other compounds with anti-convertase activity include anti-convertase antibody, either polyclonal or monoclonal, or recombinant antibody. Preferably these antibodies will be humanized antibodies. Monoclonal antibody to the convertase may be produced using the general procedures described by Kohler, G. and Milstein, C., 1975, *Nature,* 256:495, which have been modified over the years as is known in the art. These initial studies involved fusing murine lymphocytes and drug selectable plasmacytomas to produce hybridomas. Subsequently, the technique has been applied to produce hybrid cell lines that secrete human monoclonal antibodies. The latter procedures are generally described in Abrams, P., 1986, *Methods in Enzymology,* 121:107, but other modifications are known to those skilled in the art. Regardless of whether murine or human antibody is produced, the antibody-secreting cells are combined with the fusion partner and the cells fused with a suitable fusing agent, preferably polyethylene glycol, and more preferably polyethylene glycol 1000. The latter is added to a cell pellet containing the antibody-secreting cells and the fusion partner in small amounts over a short period of time accompanied with gentle agitation. After the addition of the fusing agent, the cell mixture is washed to remove the fusing agent and any cellular debris, and the cell mixture consisting of fused and unfused cells seeded into appropriate cell culture chambers containing selective growth media. After a period of several weeks, hybrid cells are apparent, and may be identified as to antibody production and subcloned to ensure the availability of a stable hybrid cell line.

A preferred antibody is human monoclonal antibody which can be produced from lymphocytes sensitized with convertase either in vivo or in vitro and immortalized as antibody-producing hybrid cell lines, thereby making available a renewable source of the desired antibody. In vitro immunization techniques are well known in the art, while in vitro techniques are generally described by Luben, R. and Mohler, M., 1980, *Molecular Immunology,* 17.635, Reading, C. *Methods in Enzymology,* 121 (Part One): 1, or Voss, B., 1986, *Methods in Enzymology,* 121:27. A number of in vitro immunization systems have been shown to be effective for sensitizing human B-cells. Reading, C., 1982, *J. of Immun. Methods,* 53:261.

It will be apparent to those skilled in the art, that in lieu of immunizing individuals directly with TNF convertase, lymphocytes may be isolated from individuals that are experiencing, or have experienced a bacteremic attack. For example, human patients having Wegener's granulomatosis are natural source of anti- PR-3 antibodies and also contain human cells suitable for deriving human monoclonals. A fraction of these lymphocytes will be sensitized to the convertase and may be used to produce permanent antibody-secreting hybrid cell lines. For example, immunocompromised human patients are generally susceptible to bacterial infections, particularly those suffering from various malignancies, extensive burns, etc., and lymphocytes isolated therefrom may be a source of antibody-secreting cells.

Sensitized lymphocytes can be immortalized by viral transformation. The preferred viral transformation technique for human lymphocytes involves the use of Epstein-Barr virus. The virus is capable of transforming human B-cells, and has been used to generate human monoclonal antibodies. Crawford, D. et al., 1983, *J. of General Virology,* 64:697; Kozbor, V. and Roder, J., 1983, *J. Immun. Today,* 4:72.

Another procedure whereby sensitized lymphocytes may be immortalized consists of a combination of the above two techniques, that is viral transformation and cell fusion. The preferred combination consists of transforming antibody-secreting cells with Epstein-Barr virus, and subsequently fusing the transformed cells to a suitable fusion partner. The fusion partner may be a mouse myeloma cell line, a hetero-myeloma line, or a human myeloma line, or other immortalized cell line. PCT No. 81/00957; Schlom et al., 1980, *PNAS (USA),* 77:6841; Croce et al., 1980, *Nature,* 288:488. The preferred fusion partner is a mouse-human hetero-hybrid, and more preferred is the cell line designated F3B6. This cell line is on deposit with the American Type Culture Collection, Accession No. HB8785. It was deposited Apr. 18, 1985. The procedures for generating F3B6 are described in EPA No. 174,204.

Techniques applicable to the use of Epstein-Barr virus transfornation and the production of immortal antibody-secreting cell lines are presented by Roder, J. et al., 1986, *Methods in Enzymology,* 121:140. Basically, the procedure consists of isolating Epstein-Barr virus from a suitable source, generally an infected cell line, and exposing the target antibody-secreting cells to supernatants containing the virus. The cells are washed and cultured in an appropriate cell culture medium. Subsequently, virally transformed cells present in the cell culture can be identified by the presence of the Epstein-Barr viral nuclear antigen, and transformed antibody-secreting cells can be identified using standard methods known in the art.

It will be apparent to those skilled in the art that while a preferred embodiment of the instant invention is a neutralizing anti-TNF convertase monoclonal antibody, singly or in combination, that the antibody(s) may be altered and still maintain biological activity. Thus, encompassed within the scope of the invention is antibody modified by reduction to various size fragments, such as F(ab')$_2$, Fab, Fv, or the like. Also, the hybrid cell lines that produce the antibody may be considered to be a source of the DNA that encodes the desired antibody, which may be isolated and transferred to cells by known genetic techniques to produce genetically engineered antibody. An example of the latter would be the production of single-chain antibody having the antibody combining site of the hybridomas described herein. Single-chain antibodies are described in U.S. Pat. No. 4,704,692. A second example of genetically engineered antibody is recombinant, or chimeric antibody. Methods for producing recombinant antibody are shown in U.S. Pat. No. 4,816,567, to Cabilly, et al.; Japanese Patent Application No. 84169370, filed Aug. 15, 1984; U.S. Ser. No. 644,473, filed Aug. 27, 1984; British Patent Application No. 8422238, filed on Sep. 3, 1984; Japanese Patent Application, No. 85239543, filed Oct. 28, 1985; U.S. Ser. No. 793,980 on Nov. 1, 1985; U.S. Ser. No. 77,528, filed Jul. 24, 1987. Also, British Patent Application No. 867679, filed Mar. 27, 1986 describes methods for producing an altered antibody in which at least parts of the complementary determining regions (CDRs) in the light or heavy chain variable domains have been replaced by analogous parts of CDRs from an antibody of different specificity. Using the procedures described therein, it is feasible to construct recombinant antibody having the CDR region of one species grafted onto antibody from a second species that has its CDR region replaced. The preferred embodiment in this instance is a murine anti-convertase antibody CDR region that replaces the CDR region of human antibody.

In addition to antibodies, compounds that compete with 26 kD proTNF (SEQ ID NO:2) for binding to the convertase will inhibit or reduce the conversion of 26 kD proTNF to the mature form, and may thus be useful medicaments for treating sepsis and other diseases. One such class of reagents consists of peptides, polypeptides, or proteins, or other compounds synthetic, or naturally occurring, that have TNF convertase-binding activity similar to or better than the 26 kD proTNF. Preferred peptides (SEQ ID NOS:5, 7, 9, 10 and 13) or proteins are those that contain amino acid sequences similar to that found at the junction between the 76 amino acid leader sequence of proTNF and the 17 kD mature form. On such sequence is Leu-Ala-Gln-Ala-Val-Arg-Ser-Ser-Ser (SEQ ID NO:13), where the second Ala is the residue present on the leader remaining in the membrane after the cleavage event, and Val is the N-terminal amino acid of the mature TNF. It is important to note that while the sequence is shown to consist of nine amino acids, that what is minimally intended is a peptide containing at least the dipeptide sequence Ala-Val that is recognized by the convertase.

An alternate embodiment of a peptide/protein convertase inhibitor is one that has the amino acid sequence, a sequence that is functionally similar to (SEQ ID NO:5). This peptide spans two TNF convertase cleavage sites, and thus would prevent the formation of the 17 kD mature TNF, among others. The first and dominant cleavage site is between alanine and valine at positions −1 and +1; and secondary sites are between valine and arginine at positions +1 and +2, and proline and valine at positions +12 and +13. These positions correspond to the amino acid sequence shown in FIG. 1.

A second class of competitive inhibitors consists of compounds including the sequence shown above, that is (SEQ ID NO:5), but wherein certain amino acids have been altered or deleted to yield a non-cleavable substrate. A preferred embodiment of this peptide is a 26 kD proTNF mutein produced by standard site-specific mutagenesis techniques. Most preferred is a mutein wherein the (−1) alanine or (+1) valine or both are substituted or deleted.

The peptides described above can be made by techniques well known in the art, such as, for example, the Merrifield solid-phase method described in *Science,* 232:341–347 (1985). The procedure may use commercially available synthesizers such as a Biosearch 9500 automated peptide machine, with cleavage of the blocked amino acids being achieved with hydrogen fluoride, and the peptides purified by preparative HPLC using a Waters Delta Prep 3000 instrument, on a 15–20 μm Vydac C4 PrepPAK column.

The peptide diphenyl phosphonates described above are also used as inhibitors. Useful peptides may be attached to Boc and the diphenyl phosphonate moiety (see Oleksyszyn et al., 1991, *Biochem.,* 30:485) and tested in a convertase inhibition assay. Preferred peptides are Boc-Val-Pro-Val-p (OPh)$_2$, Boc-Ala-Pro-Val-p(OPh)$_2$, and Boc-Val-Pro-His-p (OPh)$_2$. However, it will be seen that other peptide diphenyl phosphonates may be used in the inhibition assays described below to identify further TNF convertase inhibitors. Examples are disclosed below and are shown in Oleksyszyn et al., 1991, *Biochem.,* 30:485.

The specificity of the identified TNF convertase PR-3 is similar to enzymes such as eastase, which typically cleave immediately following certain neutrally charged amino acids, such as between valine, proline, and alanine residues. Thus, in addition to the peptide inhibitors mentioned above, a variety of other inhibitors known to inhibit elastase may also generally inhibit an enzyme that cleaves the 26 kD proTNF (SEQ ID NO:2). Those compounds that inhibit TNF convertase can be identified using the assays described below. A variety of elastase inhibitors are commercially available from suppliers such as Boehringer Mannheim Biochemicals, or are known in the art. Doherty, et al., 1986, *Nature,* 322:192; U.S. Pat. Nos. 4,711,886, 4,797,396; 4,717,722; and 4,699,904. The preferred elastase inhibitors are modified cephalosporin antibiotics, such as those shown by Doherty, et al., above. More preferred is (1-((3-((acetyloxyl)-7-methoxy-8-oxy-8-oxo-5-thio-1-azabicyclo [4.2.0] oct-2-en- $^2$-yl) carbonyl) morpholine, S,S-dioxide, (6R-cis). Also, Stetler, et al., 1986, *Nucleic Acids Research,* 14:7883, describe a cDNA clone that codes for an inhibitor of neutrophil elastase. However, preferred inhibitors are those which inhibit PR-3 more effectively than elastase, since elastase activity may help ameliorate septic shock by, for example, degrading circulating TNF or releasing soluble TNF receptors which, in turn, inhibit circulating TNF. (See Scuderi, 1991, *Cellular Immunology,* 135:299–313).

Additionally, inhibitors may be found by modeling the crystal structure for PR- 3 (SEQ ID NO:4) by adapting the known structure for the closely homologous elastase molecule. Computer models known in the art may be constructed to establish important contact points in the substrate-binding site of PR-3. Potential inhibitors may be designed based on this information and then tested in the present assay systems, as well as in relevant animal models for septic shock.

Recombinant techniques may be used to obtain the inhibitors, the proTNFs, mature TNFs or TNF convertases described herein. Most of the recombinant techniques that are described herein that may be used to transform cells, fabricate vectors, extract messenger RNA, and the like are widely practiced in biotechnology and most practitioners are familiar with the standard materials and methods employed. However, for convenience, the following paragraphs are offered as a guideline.

A. General Cloning Techniques

Construction of suitable vectors containing the desired TNF coding sequence employs standard ligation and restriction techniques which are well understood in the art. Isolated vectors, DNA sequences, or synthesized oligonucleotides are cleaved, tailored, and religated in the form desired.

Site-specific DNA cleavage is performed by treating with suitable restriction enzyme(s) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution. In the examples herein, typically, an excess of restriction enzyme is used to ensure complete digestion of the DNA substrate. Incubation times of about 1–2 hours at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by chromatography using a Sephadex G-50 spin column. If desired, size separation of the cleaved fragments may be performed by polyacrylamide gel or agarose gel electrophoresis using standard techniques. A general description of size separations is found in *Methods in Enzymology,* 1980, 65:499–560.

Restriction cleaved fragments may be blunt-ended by treating with the large fragment of *E. coli* DNA polymerase I, that is, the Kienow fragment, in the presence of the four deoxynucleotide triphosphates (dNTPs) using incubation times of about 15–25 minutes at 20–25° C. in 50 mM Tris pH 7.6, 50 mM NaCl, 6 mM MgCl$_2$, 6 mM DTT and 10 mM dNTPs. After treatment with Klenow, the mixture is extracted with phenol/chloroform and ethanol precipitated. Treatment under appropriate conditions with S1 nuclease results in hydrolysis of single-stranded portions.

Ligations are performed in 15–30 µl volumes under the following standard conditions and temperatures: 20 mM Tris-Cl pH 7.5, 10 mM MgCl$_2$, 10 mM DTT, 33 µg/ml BSA, 10 mM-50 mM NaCl, and 1 mM ATP, 0.3–0.6 (Weiss) units T4 DNA ligase at 4° C. for "sticky end" ligation, or for "blunt-end" ligations. Intermolecular "sticky end" ligations are usually performed at 33–100 µg/ml total DNA concentration. In blunt-end ligations, the total DNA concentration of the ends is about 1 µM.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na+ and Mg$^{+2}$ using about 1 Unit of BAP per µg of vector at 60° C. for about 1 hour. Nucleic acid fragments are recovered by extracting the preparation with phenol/chloroform, followed by ethanol precipitation. Alternatively, religation can be prevented in vectors which have been double-digested by additional restriction enzyme digestion of the unwanted fragments.

In the constructions set forth below, correct ligations are confirmed by first transforming the appropriate *E. coli* strain with the ligation mixture. Successful transformants are selected by resistance to ampicillin, tetracycline or other antibiotics, or using other markers depending on the mode of plasmid construction, as is understood in the art. Miniprep DNA can be prepared from the transfornants by the method of Ish-Howowicz et al., 1981, *Nucleic Acids Res.,* 9:2989, and analyzed by restriction and/or sequenced by the dideoxy method of Sanger et al., 1977, *PNAS (USA),* 74:5463 as further described by Messing et al., 1981, *Nucleic Acids Res.,* 2:309, or by the method of Maxam et al., 1980 *Methods in Enzymology,* 65:499.

Host strains used in cloning in M13 consist of *E. coli* strains susceptible to phage infection, such as *E. coli* K12 strain DG98. The DG98 strain has been deposited with ATCC Jul. 13, 1984 and has Accession No. 1965.

Depending on the host cell used, transformation is done using standard techniques appropriate to such cells. Calcium treatment employing calcium chloride, as described by Cohen, 1972, *PNAS (USA)* 69:21 10, or the RbCl$_2$ method described by Maniatis et al., 1984, *Molecular Cloning: A Laboratory Manual,* Cold Spring Harbor Press, p. 254, may be used for procaryotes. Transfection may also achieved using a modification of the calcium phosphate precipitation technique of Graham et al., 1973, *Virology,* 52:456 or Wigler et al., 1978, *Cell,* 14:725.

B. Oligonucleotide Probes

Synthetic oligonucleotides are prepared by the triester method of Matteucci et al., 1981, *J. Am Chem. Soc.,* 103:3185 or using commercially available automated oligonucleotide synthesizers. Kinasing of single strands prior to annealing or for labeling is achieved using an excess, e.g., approximately 10 Units of polynucleotide kinase to 0.1 nmole substrate in the presence of 50 mM Tris, pH 7.6, 10 mM MgCl$_2$, 5 mM dithiothreitol, 1–2 mM ATP, 1.7 pmoles $\gamma^{32}$P-ATP (2.9 mCi/mmole), 0.1 mM spermidine, 0.1 mM EDTA.

C. Mutagenesis

Mutagenesis can be carried out using any number of procedures known in the art. These techniques are described by Smith, 1985, *Annual Review of Genetics,* 19:423, and modifications of some of the techniques are described in *Methods in Enzymology,* 154. part E, (eds.) Wu and Grossman (1987), chapters 17, 18, 19, and 20. The preferred procedure is a modification of the gapped-duplex site-directed mutagenesis method. The general procedure is described by Kramer et al., in chapter 17 of the *Methods in Enzymology,* above.

Conventional M13 mutagenesis methods involve annealing a short synthetic oligonucleotide to single stranded M13 DNA having a cloned target coding sequence that is sought to be mutagenized. The oligonucleotide is almost, but not entirely complementary to the target sequence and has at least one mispaired nucleotide. After the annealing reaction, the remaining portion of the single stranded DNA must be filled in to give heteroduplex DNA that can be transfected into a suitable host cell which allows for the expression of the mutation. In the gapped-duplex method, a partial DNA duplex is constructed that has only the target region exposed, unlike the conventional methods which have the target region and the rest of the single-stranded M13 DNA exposed. Like the conventional methods, a short oligonucleotide is annealed to the target region, and extended and ligated to produce a heteroduplex. However, because only a small portion of single-stranded DNA is available for hybridization in the gapped- duplex method, the oligonucleotide does not anneal to undesired sites within the M13 genome. Further, this method has the additional advantage of introducing fewer errors during the formation of the heteroduplex since only a very small region of DNA on either side of the target region has to be filled in.

More specifically, the gapped-duplex method involves cloning the target DNA sequence into an appropriate M13 phage that carries selectable markers, such as for example the stop codon amber mutation. The latter allows for negative selection in a host cell that cannot suppress the effects of the mutation. Preferably the phage is M13mp9 which contains two amber codons in critical phage genes. Thus, the sequence that encodes 26 kD proTNF is cloned into M13mp9 amber+, and single-stranded DNA is prepared therefrom using standard techniques. Next, double-stranded replicative form DNA from M13 GAP, a genetically engineered M13 derivative that lacks the amber codons is cleaved with HincII restriction enzyme. The base sequence of M13 GAP is similar to M13mp18, which lacks both the amber codons and the sequence between base pairs 6172 and 6323. This deletion flanks the multiple cloning sites of the Ml 3mp series and generates a unique HincII site. Gapped-duplex DNA is formed, using standard DNA/DNA hybridization techniques, consisting of single- stranded DNA having the amber codons, and a second strand of DNA from HincII digested M13 GAP lacking both the amber codons and the TNF coding sequences. Thus, the only portion of the gapped-duplex that is exposed is the 26 kD proTNF target sequence. The desired oligonucleotide is annealed to the gapped-duplex DNA, and any remaining gaps filled in with DNA polymerase and the nicks sealed with DNA ligase to produce a heteroduplex. The latter is transfected, preferably into a mismatch repair deficient host, and mixed phage produced. From the mixed phage population, phage carrying unmutated 26 kD proTNF DNA, which also have the amber mutations, can be selected against by infecting the mixed phage population into a host cell that cannot suppress the amber mutation. Clones can then be screened for phage that carry the desired TNF mutation.

IV. Methods of Use of TNF Convertase Inhibitors

Compounds identified as having TNF convertase-inhibitory activity will also have prophylactic or therapeutic applications in the treatment of sepsis. Because the onset of sepsis is associated with an increase in circulating mature TNF, these inhibitors may be used prophylactically in those instances where there is a risk of bacterial infection, particularly in a pre-operative setting. Similarly, when there is an early diagnosis of sepsis, the inhibitors will have beneficial therapeutic effects in substantially reducing the amount of the soluble, 17 kD form of TNF (residues 1–15 7 of (SEQ ID NO:2) that is produced.

Increases in circulating mature TNF are also associated with the diseases rheumatoid arthritis, cachexia, cerebral malaria and graft-versus-host disease. Thus, the inhibitors of this invention will also have useful prophylactic or therapeutic applications in the treatment of these diseases.

Another medical application for inhibitors of convertase is for the treatment of AIDS. It has been shown that TNF causes the activation of latent human immunodeficiency virus. Folks et al, 1989, *PNAS (USA),* 86:2365. Thus, preventing or inhibiting the formation of mature TNF, by inhibition of TNF convertase would be a valuable treatment for ADS, and would preferably be used to treat patients that are infected with the virus that is in a latent phase.

The inhibitors of this invention may be administered at concentrations that are therapeutically effective for prevention of sepsis, ADS, etc. To accomplish these goals, the peptides and chemical compounds are administered parenterally (i.e., via intravascular [intraarterial or intravenous], intramuscular, or subcutaneous routes). Methods to accomplish this administration are known to those of ordinary skill in the art.

Before administration to patients, formulants or pharmaceutically acceptable excipients may be added to the peptides and chemical compounds. A liquid formulation is preferred. For example, these formulants may include oils, polymers, vitamins, carbohydrates, amino acids, buffers, albumin, surfactants, or bulking agents. Preferably carbohydrates include sugar or sugar alcohols such as mono-, di-, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcelloluose, or mixtures thereof. Sugar alcohol is defmed as a $C_4$ to $C_8$ hydrocarbon having an -OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar.

Surfactants that can be added to the formulation are shown in EP Nos. 270,799 and 268,110.

Additionally, the present peptides and chemical compounds can be chemically modified by covalent conjugation to a polymer to increase their circulating half-life, for example. Preferred polymers, and methods to attach them to peptides, are shown in U.S. Pat. Nos. 4,766,106, 4,179,337, 4,495,285, and 4,609,546 which are all hereby incorporated by reference in their entireties. Preferred polymers are polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor.

Water-soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG conjugates is found in U.S. Pat. No. 4,766,106, both of which are hereby incorporated by reference in their entireties.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution or sterile saline, for example) which may include additional ingredients. Upon reconstitution, the composition is preferably administered to subjects using those methods that are known to those skilled in the art.

Insoluble inhibitors can be formulated by combination with one or more solubilizers. Preferred solubilizers include: ethanol; oils, such as corn oil; PEG; propylene glycol; and non-ionic surfactants. Preferred co-solvents have a molecular weight between 50 and 1,000, more preferably between 100 and 600. Preferably their concentration is between 1 and 75% w/w, more preferably between 10 and 50%. The concentration of ethanol is preferably between 0.1% and 20%, more preferably between 1 and 5%. Preferred non-ionic surfactants have a hydrophile-lipophile balance between 14 and 40, more preferably between 15 and 20, most preferably between 17 and 19. Preferably, the non-ionic surfactants have a molecular weight in the range between 100 and 250,000, more preferably between 4,000 and 200,000, most preferably between 6,000 and 150,000. Preferably, the non-ionic surfactants are effective in the concentration range of 0.005% to 10% w/v, more preferably in the range of 0.01 to 5% w/v, most preferably in the range of 5 to 2.5% w/v. Preferably, the non-ionic surfactants include those commonly used in the pharmaceutical, food, and cosmetic industries. Preferred non-ionic surfactants include: polyoxyethylene sorbitan fatty acid esters (i.e., Tweens), polyethylene glycol esters, polyethylene fatty acid esters, block copolymers of ethylene oxide and propylene oxide (i.e., Pluronics), ethylated fatty alcohol ethers (i.e., laureth-12), octylphenoxy polyethyoxy ethanol compounds (i.e., Tritons), and polyoxyethylated castor oil (i.e., Cremophor). These non-ionic surfactants can be produced by means known in the art or purchased from commercial suppliers.

Other non-ionic surfactants can be determined by using the present screening method. In this method a non-ionic surfactant is added to an insoluble inhibitor. The resulting solution is mixed or homogenized and allowed to stand for 24 hours at room temperature. If the inhibitor remains in solution, as measured by RP-HPLC, GC, or visual or spectrophotometric clarity, then the surfactant is useful to solubilize the inhibitor.

Having generally described what the applicants believe their invention to be, presented below are examples that are illustrative of the scope of the invention. It will be appreciated by those skilled in the art that the examples are not intended to be construed as limiting the invention to the materials and methods shown as there are numerous substitutions that can be made therein without departing from the scope of the invention.

EXAMPLE 1

Isolation and Identification of a TNF Convertase

HL60 cells were obtained from the American Type Culture Collection (Rockville, MD) and grown in T-175 flasks containing RPMI 1640 medium supplemented with 20% fetal bovine serum (GIBCO) and L-glutamine. Batches totalling 3 liters of HL60 cells were grown to confluency and harvested. The cells were resuspended in approximately 120 ml of a hypotonic buffer and lysed by nitrogen cavitation (400 psi, 30 minutes at 4° C.). The homogenate was centrifuged at 10,000 x g for 10 minutes, and both the supernatant and the cell debris pellet were stored at −20° C.

HL60 cell debris from 3 batches of HL60 cell cultures were thawed in 250 ml of 10 mM Tris pH 8.5 containing 0.5% NP-40, 5 mM EDTA, and 2 µg/ml leupeptin (DEAE buffer) and dialyzed for 4 hours in the same buffer. The protease inhibitors used during purification were shown to have no effect on the convertase activity detected in HL60 lysates. Particulates were removed by centrifugation (10,000×g, 10 minutes) and the sample fractionated by anion exchange chromatography on a DEAE-Sepharose column (2.6×21 cm, Pharmacia) eluted with a 680 ml, NaCl gradient from 0–0.8 M. Fractions containing TNF convertase activity were identified throughout the purification using the $^{35}$S-proTNF convertase assay. Pooled DEAE fractions were dialyzed into 20 mM sodium phosphate buffer, pH 6.5, containing 01% NP-40, 1 mM EDTA, and 1 µg/ml leupeptin, divided into three equal portions and each subjected to cation exchange HPLC on a TSK-SP-SPW column (7.5×75 mm, BioRad) eluted with a 45-minute, sodium chloride gradient from 0–0.6 M. Fractions enriched in convertase avity were pooled and dialyzed into DEAE buffer containing 0.1 % NP-40. The pooled material from the SP column was divided into three portions, and each was subjected to anion exchange HPLC on a TSK-DEAE-5PW column (7.5×75 mm, BioRad) eluted with a 45-minute, sodium chloride gradient from 0–0.6 M. The pool of convertase activity was further purified by RP-HPLC on a Vydac C4 column using an acetonitrile/0.1% TFA mobile phase.

This treatment provided a 1,000-fold purification, resulting in 20 μg of convertase (approximately 320 Units) at an 18% yield. Fractions from the RP-HPLC were tested for convertase activity and sized on SDS-PAGE. The fraction that contained convertase activity contained a protein having a molecular mass of approximately 28–31 kD. The convertase was sequenced, and an 18-amino-acid sequence at the N-terminus proved to be identical to that of the serine protease PR-3. PR-3 was subsequently isolated from human neutrophils, essentially using published procedures, and it was found to have the same activity as TNF convertase in the $^{35}$S-proTNF assay.

The identification of PR-3 as a TNF convertase was further strengthened by N-terminal sequencing of cyanogen bromide cleavage fragments, as well as amino acid composition of PR-3 both of which agreed (within experimental error) with the published amino acid sequence of mature, active PR-3 (Campanelli et al., 1990, *J. Exp. Med.*, 172:1709–1715).

EXAMPLE 2

Cloning and Recombinant Expression of Human PR-3

RNA was purified from HL60 cells and a cDNA library was constructed in the plasmid pGEM. Construction of the cDNA (SEQ ID NO:3) used C tailing of cDNA and G tailing of the vector, then ligation into the plasmid (Gene Transfer and Expression, 1990, pgs 114–135). Clones were screened using a unique oligonucleotide probe derived from the known sequence of myeloblastin (Bories et al., 1989, *Cell*, 59:959–968).

Sequencing of one clone MY17 was performed using plasmid double-strand sequencing and the Sequenase kit and an automated ABI sequencer. Sequence for MY17 is shown in FIG. 2. Novel features for the sequence include 5 nucleotide differences from the original publication by Bories et al., 1989, *Cell*, 59:959–968, and three nucleotide differences from the Campanelli et al., 1990, *J. Exp. Med.*, 172:1709–1715. Additional 5' sequence and an additional 5' methionine coding sequence was found. The two carboxyl terminal amino acids in PR-3, arginine and proline, are similar to that of Bories et al., supra, but differ from the glycine and proline sequence from Campanelli et al., supra.

Transient mammalian expression of PR-3 was performed by cloning the 1.0 Kb HinIII-EcoRI PR-3 fragment from MY17 into the PstI site of SR-α vector. COS cells were transiently transfected using the DEAE/Dextran method. Kriegler, 1990, *Gene Transfer and Expression*, pp. 99–100, Stockton Press. Transient expression revealed low levels of PR-3 expression by Western blot analysis. PR-3 was mutagenized to optimize its expression in mammalian, bacterial and insect expression systems. The PR-3 gene in the pGEM vector was mutagenized using oligonucleotide directed mutagenesis. Two constructs were made; A) delta zymogen PR-3 and B) delta signal peptide PR-3.

A) Delta zymogen PR-3 was made using an oligonucleotide that deletes the codons for amino acids at position −1 and −2 (glutamic acid and alanine, respectively). This gene can be removed from PGEM by EcoRI digestion, and the gene transferred to SR-α for transient mammalian expression and pcDNA I for production of stable transfectants.

B) Delta signal PR-3 was made using an oligonucleotide that deleted the leader and added an ATG prior to the position 1 isoleucine of the mature protein. This gene can be removed from pGEM by EcoRI digestion, and transferred to SR-α and pcDNA I for transient and stable mammalian expression. In addition, this construct was placed in DG160 a k P1 based bacterial expression vector at 8–12 nucleotides from the Shine-Dalgarno ribosomal binding site.

Another construct, the cecropin B PR-3 construct, was made so that the insect leader for cecropin B was placed before the position 1 isoleucine of the mature PR-3 protein. This was placed in the insect vector, pAcC13.

D) For optimization of bacterial expression, mutagenesis of the third nucleotide trom a purine to pyrimidine in the codons for the first 2–8 amino acids of delta signal PR-3 was performed using overlapping synthetic oligonucleotides and polymerase chain reaction amplification of the synthetic fragment. This fragment will be cloned into the 5' smal site of PR-3, to decrease the GC content of the 5' RNA and facilitate expression.

EXAMPLE 3

Conversion of 26 kD proTNF to Mature TNF

The vector pFVXM, on deposit with the American Type Culture Collection, Accession No. 67,103, was used to produce a vector pFVXM-TNF6, which contains the DNA sequence that encodes the 26 kD proTNF species. To produce the latter vector, the plasmid B11 which contains the cDNA sequence that encodes the 26 kD proTNF species was treated with PstI, which excises the coding sequence. The fragment was purified using standard electrophoretic techniques. Next, the vector pFVXM was treated with PstI, and the PstI fragment from pB11 containing the 26 kD coding sequence was inserted into the polylinker region of the vector using standard techniques, as described above, to produce pFVX-TNF6. pFVX-TNF6 was used to produce the cell line TNF 6.8, as described by Kriegler et al, 1988, above, or as described in U.S. Ser. No. 395,254, entitled "Cleavage Site Blocking Antibody to Prohormone Proteins and Uses Thereof," filed Aug. 16, 1989.

Figure 3:
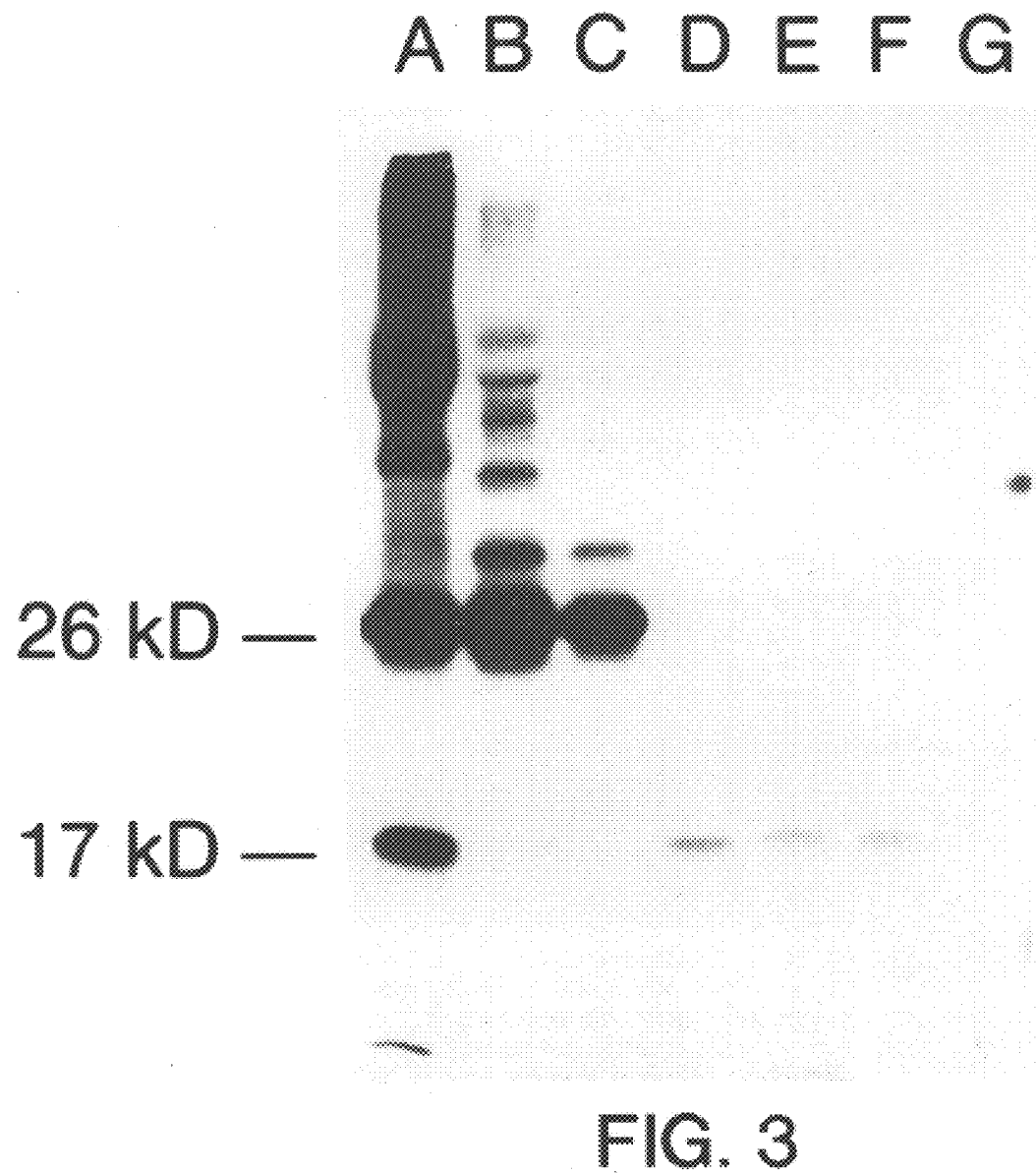
FIG. 3 shows the conversion of 26 kD proTNF by TNF convertase. Lanes A, B, and C show various controls: TNF 6.8 cell lysate (A), 26 kD transcription/translation (B) and incubation (C) controls. Lanes D, E, and F show the conversion of transcription/translation generated 26 kD proTNF to predominately 17 kD TNF by convertase present in either HL60 S-1 cytosol uninduced (D) and induced (E) fractions, or a P-1 pellet fraction prepared from induced cells. G is a blank lane.

TNF 6.8 expresses both 26 kD proTNF and 17 kD TNF (SEQ ID NO:2). FIG. 3 shows the conversion of 26 kD proTNF by convertase activity present in HL60 cells. The production of labelled 26 kD proTNF by in vitro transcription/translation, and analysis by gel electrophoresis is described below in Example 4. Note that the S-1 cytosol or pellet fractions cause the near complete conversion of 26 kD proTNF to a 17 kD species. FIG. 3 also shows, for comparative purposes, 26 kD and 17 kD proTNF in a lysate of TNF 6.8 cells.

pFVXM and the plasmid pB 11 were both amplified in *E. coli* strain HB 101. Ligation of the fragments was carried out using standard conditions. Plasmid DNA was isolated after the ligation procedure and the correct orientation of the TNF encoding sequences was established by restriction analysis.

Plasmid DNA was prepared according to the procedure of Birnboim and Doly, as described in *Nucleic Acid Research*, 7:1513 (1979). The plasmid DNA was banded twice in cesium chloride, and exhaustively dialyzed against TE buffer consisting of 10 mM Tris, pH 8.0, and 1 mM EDTA.

EXAMPLE 4

TNF Convertase Assays

A. In Vitro Transcription/Translation Assay

A preferred assay procedure consists of in vitro transcription/translation to produce the 26 kD molecule (SEQ ID NO:2), followed by treatment with convertase in the presence or absence of compounds being tested for convertase inhibitory activity. The procedure entails in vitro transcription/translation of the TNF cDNA present in the plasmid B11. Thus, the sequence was removed from pB11 by PstI digestion and was inserted into the PstI site of pGEM-3 (obtainable from Promega Biotec). The resulting plasmid, termed PEM-TNF14, was amplified in E. coli using established techniques, and plasmid DNA was prepared according to the procedure of Birnboim and Doly, described above. Plasmid DNA was in vitro transcribed by linearizing it with HindII, and the linearized plasmid templates used to prepare capped transcripts with T7 RNA polymerase and an in vitro transcription kit supplied by Promega Biotec. Transcription was performed using standard techniques as suggested by the manufacturer's instructions.

The mRNA was translated in vitro in the presence of $^{35}$S-cysteine to produce $^{35}$S-cysteine-labeled 26 kD proTNF. A rabbit reticulocyte lysate translation kit was used, also supplied by Promega Biotec, and the conditions recommended by the manufacturer were followed. $^{35}$S-cysteine-labelled 26 kD proTNF was used to assay for convertase inhibitors as follows. 25 μl of in vitro translated material was combined with 250 μl of convertase activity partially purified from uninduced HL60 cells, plus compounds to be assayed for inhibitory activity. The convertase was produced by harvesting 2×10$^9$ HL60 cells, and isolating S-1 and P-30 fractions totalling 18 and 6 ml, respectively. 250 γ of the P-30 fraction was used, although the S-1 fraction may also be used. The assay was carried out at 30° C. for 1 hour, essentially as described above. Next, the reaction mixture was immunoprecipitated with anti-TNF polyclonal antisera and protein A Sepharose, pelleted and washed. The bound protein was eluted and electrophoresed using SDS-PAGE. The gel was fixed in 40% methanol, 10% acetic acid, soaked in Enlightening (Dupont), dried, and exposed to x-ray film which was subsequently developed. The gel electrophoretic profiles of 26 kD proTNF treated with HL60 convertase and varying dilutions of the potential inhibitory compound, revealed those compounds with inhibitory activity.

Figure 4A:
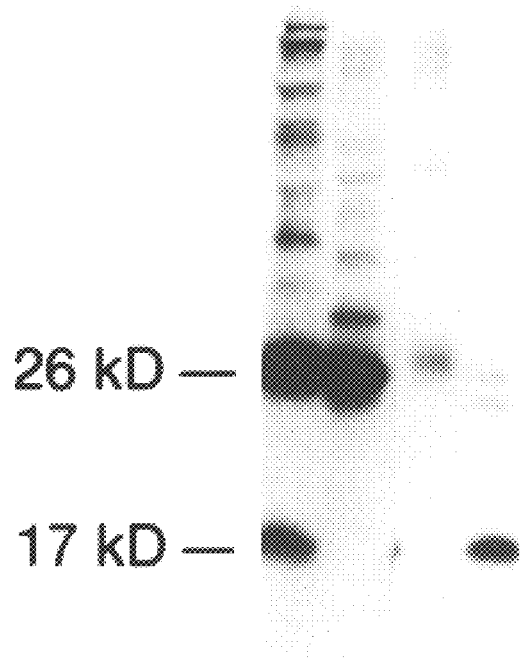
FIGS. 4A and 4B show the effect of convertase inhibitors on the conversion of 26 kDpro TNF to its lower molecular weight forms as determined by gel electrophoresis. Lanes A,B,C,and D of FIG. 4A show, respectively; immunprecipitation of a cell lysate of the pFVXM-TNF6 transfected cell line TNF 6.8 (Kriegler, et al., 1988, in Cell, 53:45), immunprecipitation of in vitro transcribed/translated 26 kD proTNF, the effect of (1-((3-((acetyloxyl)-7-methoxy-8-oxy-8-oxo-5-thio-1-azabicyclo [4.2.0] oct-2-en- 2-yl) carbonyl) morpholine, S,S-dioxide, (6R-cis) on the conversion of 26 kD proTNF, and the conversion of 26 kD proTNF in the absence of (1-((3-((acetyloxyl)-7-methoxy-8-oxy-8-oxo-5-thio- 1-azabicyclo [4.2.0] oct-2-en- 2-yl) carbonyl) morpholine, S,S-dioxide, (6R-cis). Lanes A and B of FIG. 4B show, respectively; immunprecipitation of a cell lysate of the pFVXM-TNF6 transfected cell line TNF 6.8 (Kriegler, et al., 1988, in Cell, 53:45), and immunprecipitation of in vitro transcribed/translated 26 kD proTNF. Lanes C and D show the conversion of 26 kD proTNF in the presence and absence of 3,4-dichloro-isocoumarin, respectively. Lanes E and F, show the conversion of 26 kDpro TNF in the presence and absence of elastinal, respectively.
Figure 4B:
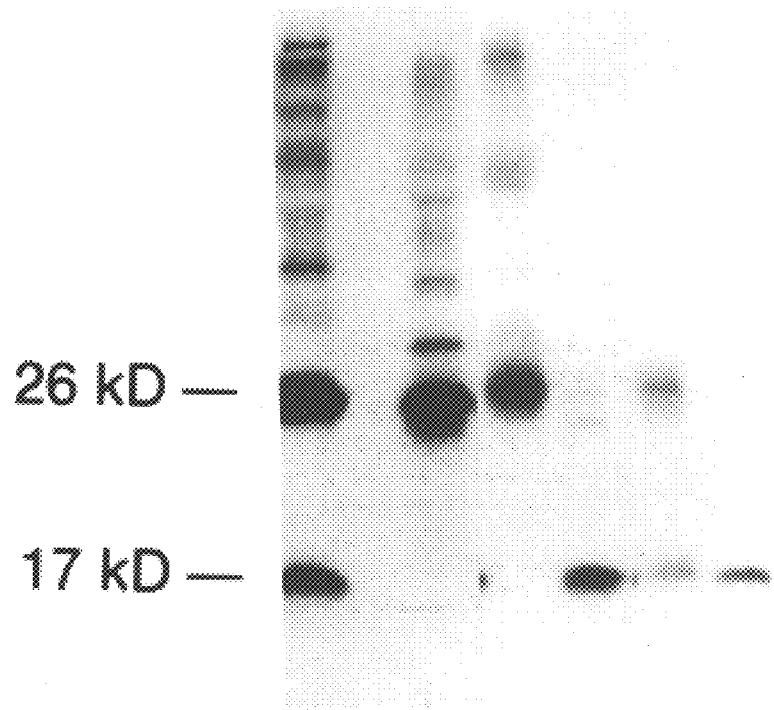

Using the above assay, it was determined that 3,4-dichloro-isocoumarin and elastinal at concentrations of 100 μg/ml and 5 mg/ml, respectively, inhibit the convertase. It was also shown that (1-((3-((acetyloxyl)-7-methoxy-8-oxy-8-oxo-5-thio-1-azabicyclo [4.2.0] oct-2-en- 2-yl) carbonyl) morpholine, S,S-dioxide, (6R-cis) at a concentration of 1 mM inhibits convertase activity. These results are shown in FIGS. 4A and 4B.

Figure 5:
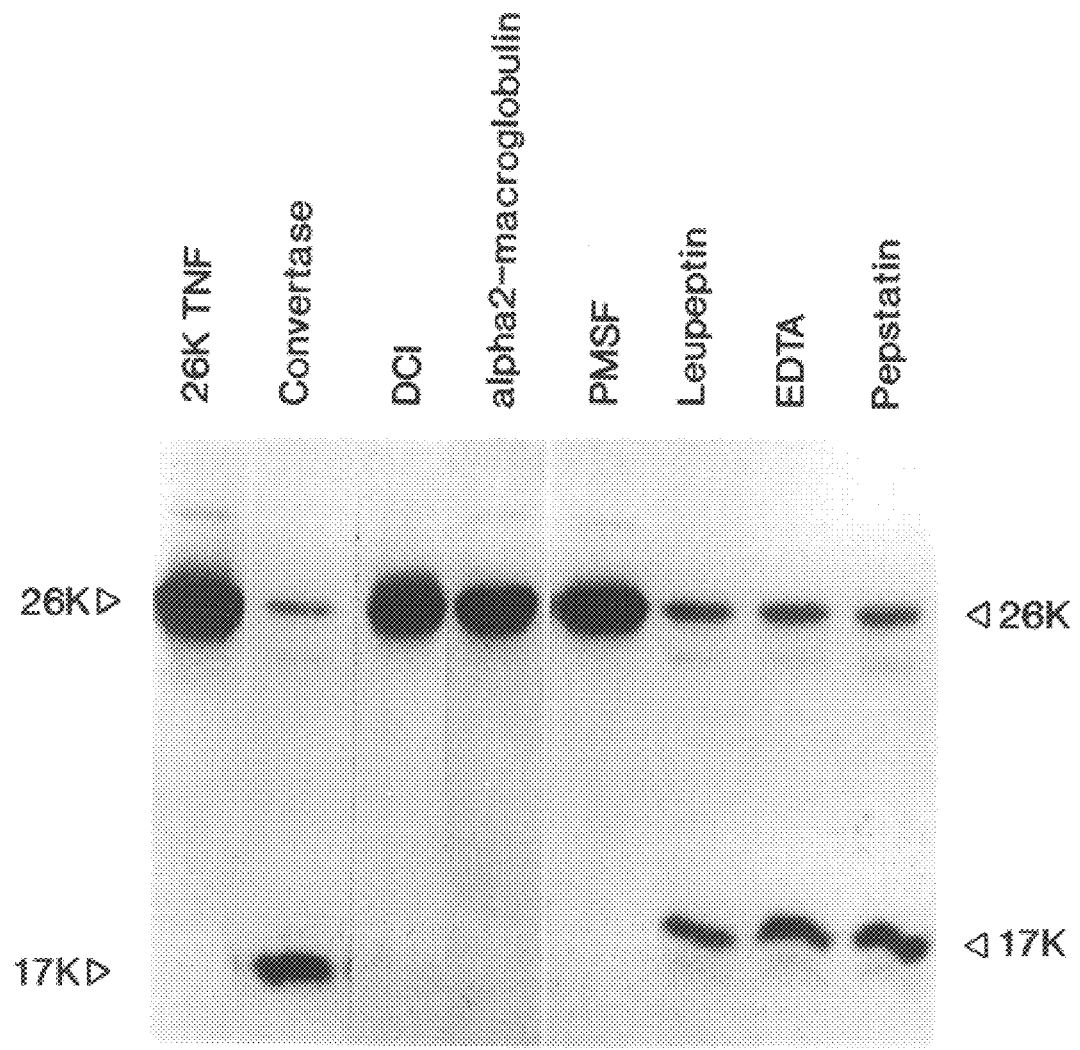
FIG. 5 shows additional gel electrophoretic assays on 26 kD proTNF, demonstrating inhibition of purified human PR-3 from HL-60 cells by various serine protease inhibitors.

The above assay was also used with pure HL60 cell PR-3 (SEQ ID NO:4) to test a variety of proteinase inhibitors for TNF convertase inhibitory activity, as shown in FIG. 5. Pure PR-3 (0.3 μg/ml) (SEQ ID NO:4) was preincubated for 30 minutes with the following inhibitors prior to addition of $^{35}$S-labelled 26 kD proTNF and assaying as described above: DCI (45 μM), α-2-macroglobulin (1 mg/ml), PMSF (20 μM), leupeptin (2 μg/ml), EDTA (10 mM), or pepstatin (2 μg/ml). The first three of these inhibitors showed significant inhibitory activity.

B. Monocyte Assay

The 26 kD form of TNF can also be produced by stimulated monocytes which produce 26 kD proTNF, as described by Kriegler, et al., 1988, Cell, 53:45.

Briefly, human monocytes are purified from human blood by centrifugation, and subsequently enriched based on the adherence of monocytes to cell culture dishes. Centrifugation consists of purifying the monocytes through Ficoll-hypaque and percoll (49.2%), obtainable from Pharmacia. The manufacturers recommended procedures followed. Next, the mixture of cells resulting from the centrifugation step, consisting of monocytes and lymphocytes, are plated onto tissue culture dishes containing RPMI media supplemented with 20% fetal calf serum. The dishes are incubated for 30 minutes at 37° C. after which they are extensively rinsed with the same media This treatment removes non-adherent lymphocytes and leaves only adherent monocytes.

Monocyte 26 kD proTNF is radiolabelled as follows. The monocytes are incubated for 3 hours at 37° C. in RPMI media supplemented with 20% fetal calf serum, 100 ng/ml lipopolysaccharide, and 10 μg/ml phorbol myristate acetate for 30 minutes at 37° C. The latter two compounds induce the expression of TNF. The RPMI media is cysteine- minus, and the fetal calf serum present at a final concentration of 5%. The serum is dialyzed prior to use to remove any cysteine present. After the 30-minute incubation period, 100 uCi$^{35}$S-cysteine is added, and the cells are radiolabelled for 3 hours at 37° C., after which they are lysed and used to assay for convertase activity. The steps for carrying out the assay, as well as identifying inhibitors of the convertase, are similar to those described above.

C. Colorimetric Assay for Convertase Inhibition

TNF convertase inhibition can also be measured by a colorimetric assay. In this type of assay, the actual conversion of proTNF to mature TNF is measured indirectly using a colorimetric TNF convertase substrate. By "colorimetric TNF convertase substrate" is meant a compound that is cleaved by a TNF convertase to release a compound that absorbs light of a certain frequency. One such substrate is Boc -Ala-ONp (Bachem Bioscience, Inc., Philadelphia, Pa.). Other such substrates can be discerned from the structure of TNF convertase and other serine proteases. Although the example herein uses purified native PR-3 (SEQ ID NO:4) as the TNF convertase, it is contemplated that recombinant PR-3 or other TNF convertases can be used in this assay as well.

Peptide diphenyl phosphonate inhibitors were synthesized and stored as lyophilized solids as described in Oleksyszyn and Powers, 1991, Biochem., 30:485–493. Inhibitor solutions (10 mg/ml) were prepared in 100% dimethyl sulfoxide (DMSO) and diluted into aqueous buffers upon initiation of the experiments. 3,4, di-chloro-isocumarin was purchased from CalBiochem. Purified PR-3 (10 μl, 0.1 mg/ml) was mixed with varying concentrations of protease inhibitor (400 μl final volume) in 20 mM sodium phosphate buffer, pH 7.0, containing 0.1 M sodium chloride. Aliquots (40 μl) were removed at selected times and diluted ¹⁄₁₀ into a colorimetric assay for convertase, containing 0.5–1 mM BOC-Ala-ONp (prepared fresh from a 50 mM stock in 100% methanol) in 0.02 M sodium phosphate buffer, pH 7.0, 0.1 M sodium chloride. The increase in absorbance was monitored at 347 nm on a Hewlett Packard 8450A spectrophotometer, and using an extinction co-efficient of $5.5 \times 10^3$ M$^{-1}$c$^{-1}$.

EXAMPLE 5

Peptide Diphenyl phosphonate Inhibitors of TNF Convertase

Several peptide diphenyl phosphonates were tested for inhibitory activity: Boc- Val-Pro-Val-p(OPh)$_2$ (VPV), Boc-Ala-Pro-Val-p(OPh)$_2$ (APV), Boc-Ala-Gln-Ala-p(OPh)$_2$ (AQA), and Boc-Leu-Ala-Gln-Ala-p(OPh)$_2$ (LAQA) (SEQ ID NO:12). The peptides were prepared by chemical synthesis using the Merrifield method and the diphenyl phosphonates were prepared according to the method similar to the one shown in Oleksyszyn et al, supra.

Figure 6A:
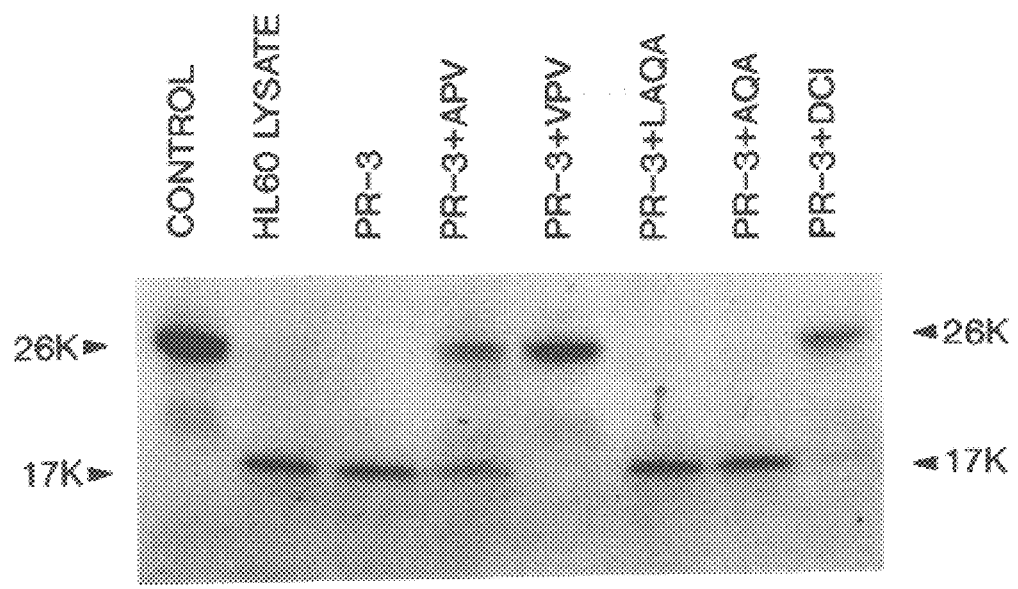
FIG. 6A shows gel electrophoretic analysis of purified human neutrophil PR-3 activity on 26 kD proTNF, showing differential inhibitory activity of potential serine protease inhibitors.
Figure 6B:
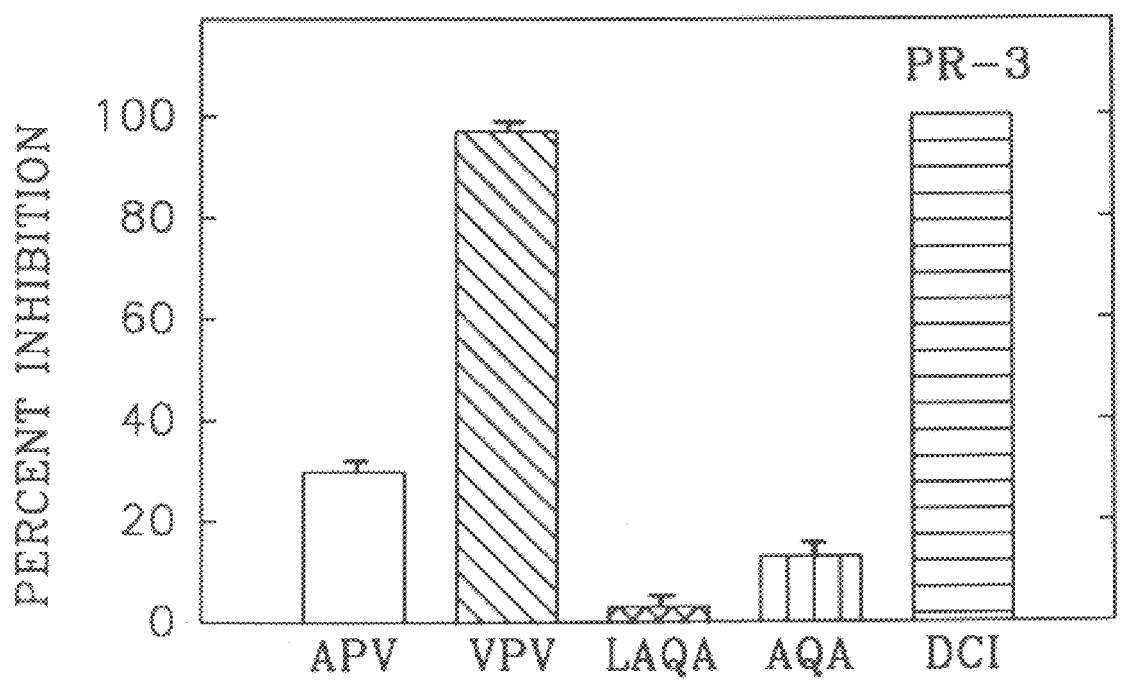
FIG. 6B shows similar results obtained using a calorimetric assay testing the same compounds.

The peptide diphenyl phosphonates were tested in the colorimetric assay described in Example 3, for inhibition of TNF convertase/PR-3 activity. The results are shown in FIG. 6. VPV and APV demonstrated inhibitory activity. AQA and LAQA showed marginal, if any inhibition at the concentrations tested Dichloro isocoumarin (DCI) showed 100% inhibition in the assay.

EXAMPLE 6

TNF Mutein/Antibody/Peptide Inhibitors of Convertase Activity

The following compounds will have convertase inhibitory activity and can be prepared as follows. These compounds may be tested for inhibitory activity as described in Example 4 above.

A. Anti-Convertase Antibody

Monoclonal or polyclonal antibody is prepared that binds to the convertase and thereby sterically prevents the convertase from binding to 26 kD proTNF (SEQ ID NO:2) or otherwise neutralizes the enzymatic activity of the convertase. The procedure consists of immunizing an appropriate host animal with a membranous fraction of HL60 cells producing TNF convertase. Alternatively, purified TNF convertase may be used from native or recombinant sources. For example, PR-3 from human neutrophils may elicit anti-TNF convertase antibodies. A sufficient amount of material should be used to elicit an immune response, and usually this will consist of between 10 µg to 10 mg per kilogram of body weighs Immunization may be conducted with adjuvant in a biologically acceptable buffer, as is known in the art. The best immunization route can be determined experimentally, and the primary immunization may be followed by one or more secondary immunizations depending on the strength of the immune response to the initial immunization. The presence of neutralizing anti-convertase antibody in the sera may be detected using the convertase assay described above wherein antisera is present in the assay mixture. Inhibition of the conversion of the 26 kD proTNF species to species having the molecular weight of mature TNF indicates the presence of a neutralizing antibody. It is, of course, assumed that the proper controls are conducted to insure that anti-sera from non-immunized animals is not inhibitory. Polyclonal antibody may be purified as described below.

Monoclonal antibody to the convertase may be produced using either in vivo or in vitro immunization techniques, and sensitized lymphocytes resulting therefrom can be used to prepare hybrid cell lines that secrete the appropriate monoclonal antibody. Rodent, preferably of murine origin, or human antibody is most preferred. The in vitro immunization procedure involves sensitizing lymphocytes to the convertase by immunizing either mice or humans, and isolating therefrom the antibody-secreting cell fraction and immortalizing the cells therein by one of several procedures. An alternate embodiment is to isolate lymphocytes that have already been sensitized to the convertase from septic patients or Wegener's granulomatosis patients as described above.

(i) Murine Antibody

For in vivo immunization of mice, the procedure of Kohler and Milstein described in *Nature,* 256:495 (1975) may be followed, or modified procedures such as those shown by Fendly et al., 1987, *Hybridoma,* 6:359; Buck,et al., 1988, *In Vitro,* 18:377. In vitro techniques are generally described by Luben, R. and Mohler, M., 1980, *Molecular Immunology,* 17:635, Reading, *Methods in Enzymology,* 121 (Part One):18, or Voss, 1986, *Methods in Enzymology,* 121:27.

Mice are immunized with 1 mg/ml of a membranous fraction of HL60 cells previously shown to be positive for convertase activity. Alternatively, a smaller amount of purified TNF convertase may be employed. The immunization is carried out in complete Freund's adjuvant. Two additional immunizations, or boosts, are performed at monthly intervals without adjuvant, and one month after the last boost the mice are given an I.V. boost of 10 µg of membranous material. Three days after the I.V. boost, mice are sacrificed, their spleens removed, and the spleenocytes isolated and fused to an immortalized drug selectable myeloma partner cell line. Numerous such myeloma lines are known in the art, most of which are incapable of growth in HAT supplemented cell culture media. A typical myeloma cell line is SP-2/0 Ag 14. Thus, the hybridomas are formed by combining splenocytes and myeloma cells in a 5:1 ratio, which generally consists of $2 \times 10^6$ myeloma cells to $1 \times 10^7$ splenocytes. The cell mixture is pelleted, media removed and fusion affected by the addition of 1.0 ml of 40% (v/v) solution of polyethylene glycol 1500 by dropwise addition over 60 seconds at room temperature, followed by a 60 second incubation at 37° C. To the cell suspension with gentle agitation is added 9 ml of Dulbecco's Modified Eagles medium over 5 minutes. Cell clumps in the mixture are gently resuspended, the cells washed to remove any residual PEG and plated in microtiter plates at about $2 \times 10^5$ cells/well in DMEM supplemented with 20% fetal calf serum. After 24 hours, the cells are fed a 2×solution of hypoxanthine and azaserine selection medium.

Media from wells that exhibit positive cell growth may be screened for neutralizing monoclonal antibody to the convertase. The preferred assay is the convertase assay described in Example 2, above, wherein media sought to be tested for antibody activity is present in the assay. More preferred is to combine culture supernatants from 3–8 microtiter wells, and assay the mixture. If the mixture is positive, then media from each well may be assayed independently to identify the secreting hybridoma(s). Many assays are known in the art and can detect soluble, or non-soluble antigens, and are shown by Langone, J. and Van Vinakis, H., *Methods of Enzymology,* 92. Part E (1983).

Regardless of whether the antibody is polyclonal or monoclonal it is desirable to purify the antibody by standard techniques as is known in the art, or described by Springer, 1980, *Monoclonal Antibodies,*:194, (Eds. Kennett, T. McKearn and K. Bechtoi, Plenum Press, New York. Generally this consists of at least one ammonium sulfate precipitation of the antibody using a 50% ammonium sulfate solution. Antibody affinity columns may also be used.

(ii) Human Monoclonal Antibody

Peripheral blood lymphocytes are isolated from septic patients, and then infected with Epstein-Barr virus and the infected lymphocytes immortalized by fusion to a selectable myeloma cell line, and the hybrid cell lines so generated isolated and characterized as to antibody production.

More specifically, mononuclear cells are separated on Ficoll-hypaque (Pharmacia), and monocytes depleted from the mixture by adherence to plastic. Standard laboratory techniques were utilized to effect these procedures. Next, nonadherent cells are enriched for antibody producers by antigen-specific panning. Panning is a technique generally known in the art, and involves incubation of a population of antibody-secreting cells on a plastic surface coated with the appropriate antigen. Those cells that express antibody on their surface bind antigen, and consequently adhere to the plastic surface, whereas cells that do not express cell surface antibody, do not adhere and can be removed by washing. Thus, specific antibody-secreting cells are enriched for by this technique.

More specifically, 6-well plates (Costar) are coated with purified TNF-convertase or a membrane fraction containing convertase prepared from either induced or uninduced HL60 cells, as described above, such that 150 µg of membranous material is coated per well in phosphate buffered saline at 4° C. overnight. The wells are blocked after the overnight incubation period with phosphate buffered saline containing 1% bovine serum albumin for at least 1 hour at 4° C., and subsequently washed with phosphate buffered saline/BSA. Next, $10^7$ lymphocytes in 1 ml of PBS/BSA are added to each well of the six well plates. The lymphocytes are allowed to incubate on the plates for 70 minutes, after which any nonadherent cells are removed by aspiration. The adherent cells are incubated with cell culture medium (IMDM, Sigma Chemical Co., St. Louis, Mo.) containing 10% fetal calf serum.

The adherent cells are subjected to Epstein-Barr virus transformation by adding an equal amount of culture media obtained from growing the Epstein-Barr virus infected marmoset cell line, B95-8, and thus containing the virus, to media bathing the adherent cells. The cells were cultured in this environment at 37° C. for 3 hours, and in this way the lymphocytes in the adherent cell population are subjected to Epstein-Barr infection. Following the infection period, the cells are washed and plated onto 96 well microtitre plates at a density of about $10^4$–$10^5$ cells/well in IMDM medium, plus 10% fetal calf serum, and 30% conditioned medium. The latter is derived from a lymphoblastoid cell line, preferably JW5. The medium also contains $5 \times 10^{-5}$ M 2-mercaptoethanol, 50 µg/ml gentamycin sulfate (Sigma), and 600 ng/ml cyclosporine A (Sandimmun, Sandoz, Basel, Switzerland).

After about 14 to 21 days of incubation, cell culture supernatants are combined and screened for TNF convertase-neutralizing activity as described above. Positive hybridomas are subcultured at low density, retested for neutralizing antibody, and grown up and fused to the cell line F3B6 using polyethylene glycol and the plate fusion technique known in the art. The latter technique is described by Larrick, 1985, in *Human Hybridomas and Monoclonal Antibodies*, E. G. Engleman, S. K. H. Foung, J. W., Larrick, and A. A. Raubitschek, Editors, Plenum Press, New York, page 446. F3B6 is a heteromyeloma cell line that is sensitive to growth in media containing 100 µM hypoxanthine, 5 µg/ml azaserine and 5 µM ouabain. Finally, the resulting hybrids are again screened to insure that they produce neutralizing anti-convertase antibody.

B. 26 kD Muteins 26 kD proTNF muteins are described that compete for binding to the convertase, thereby inhibiting or reducing its activity. The preferred mutein embodiments are those having valine at positions 1 and/or 13; or alanine at position -1 and/or proline at position 12, replaced or deleted. The muteins are constructed using a modification of the site-directed mutagenesis gapped-duplex method.

The following solutions/buffers are used to perform the desired procedures: 5×gapped-duplex buffer (GDB) consisting of 0.938 M KCl, 0.063 M Tris, pH 7.5; 10×PEL consisting of 1.0 M KCl, 0.30 M Tris, 0.15 M $MgCl_2$, 0.02 M DTT, pH 7.5; 10×KB consisting of 0.50 M Tris, 0.10 M $MgCl_2$, 0.05 M DTT, 0.001 M EDTA, pH 8.0; a solution containing 0.25 mM dCTP, dATP, dGTP, dTTP, made fresh from 10 mM stocks; an ATP solution consisting of 0.1 M ATP made by dissolving 60 mg of ATP in 0.80 ml of $H_2O$ and adjusting the pH to 7.0 with 0.1 M NaOH in a final volume of 1.0 ml with $H_2O$; 20% PEG/2.5 M NaCl; 3.0 M NaOAc; and TE-saturated phenol.

Various bacterial strains and phage are employed to yield the desired muteins and these are BMH 71–18, JM103 for growing phage strains; HB2154: MutL, Su-, made competent for DNA transformation; and HB2151: Su-, used as lawn cells during transformation; M13 GAP, the RF is used for the formation of the gapped-duplex; and M13mp19amber, the 26 kD proTNF target DNA is cloned in this vector, and ssDNA isolated for the formation of gapped-duplex.

Phage are infected into an appropriate bacterial strain, grown up, and titered as follows. In making a large-scale preparation of either phage for ssDNA or cells for dsDNA, or RF DNA, the same infection protocol is used.

Plaque-purified phage is produced using standard techniques. Briefly, this consists of streaking phage supernatants on agar plates, followed by careful overlay with 4.0 ml of soft agar and 100 µl of fresh overnight culture of BMH 71–18. Next, isolated plaques are picked and incubated with a 1:50 dilution of fresh overnight culture of BMH 71–18 in R26 or R17+10 mM MgCl2 with shaking at 37° C. for 4.5–6 hours. R17 (N-Z amine broth) consist of 10 g N-Z amine, type A, 5 g NaCl with $H_2O$ to 1 liter, while R26 consist of 8 g tryptone, 5 g yeast extract, 5 g NaCl, with water to 1 liter (YT broth). The phage stock is titered, and phage infected into bacteria at a multiplicity of infection (MOI) of 10. After incubating the culture with shaking at 37° C. for 5 hours the cell suspension is pelleted, and the supernatant saved for ssDNA isolation, and the cells for RF isolation. RF DNA is isolated using established plasmid DNA isolation techniques, while ssDNA is isolated as follows.

250 ml of phage supernatant is spun down hard, after which 200 ml of the supernatant is decanted, followed by adding 50 ml of 20% PEG/2.5 M NaCl, and incubation overnight at 4° C., or on ice for 30 minutes. This mixture is also spun down hard, and the supernatant decanted. The bottle is spun again to pellet the phage precipitate along the sides of the bottle, and the remaining fluid aspirated with a Pasteur pipette. The pellet is resuspended in 5.0 ml of 1×TE, and stored at 4° C., after which 0.5 ml of is extracted twice with 0.5 ml of TE saturated phenol. To the aqueous layer is added 0.050 ml of 3.0 M NaOAc and 1.0 ml 95% ethanol. The mixture is placed in a dry ice bath for 10 minutes, and centrifuged for 10 minutes in a microfuge at 4° C. The pellet is dried, and resuspended in 200 µl of 1×TE. This material may be stored in 0.050 ml aliquots at −20° C. until used in the mutagenesis of 26 kD proTNF.

The following deletions and substitutions in Table 1 are preferred proTNF muteins. These muteins can be prepared using appropriate oligonucleotides by methods known in the art.

TABLE 1

| |
|---|
| Deletions |
| ΔVAL 1 |
| ΔVAL 13 |
| ΔVAL 1 + ΔPRO 12 |
| ΔVAL 1 + ΔVAL 13 |
| Substitutions |
| (VAL 1 → ALA 1) + (VAL 13 → ALA 13) |
| (VAL 1 → GLY 1) + (VAL 13 → GLY 13) |

TABLE 1-continued (VAL 1 → LEU 1) + (VAL 13 → LEU 13)
(VAL 1 → MET 1) + (VAL 13 → MET 13)
(VAL 1 → PHE 1) + (VAL 13 → PHE 13)
(VAL 1 → HIS 1) + (VAL 13 → HIS 13)
(VAL 1 → THR 1) + (VAL 13 → THR 13)
(ALA 1, VAL 1 → GLN 1, HIS 1) + (PRO 12, VAL 13 → GLN 12, HIS 13)
(ALA 1, VAL 1 → GLN 1, HIS 1) + (PRO 12, VAL 13 → SER 12, THR 13)

The oligonucleotides are kinased using the following reaction solution and conditions: 3 µl 10×KB buffer, 3γ10 mM rATP (1:10 dilution of 0.1 M rATP stock), 2 γ mutagenic oligonucleotide (100 pmole/γ), 21 γH$_2$O, and 1 γ polynucleotide kinase (10 Units/X). The reaction is run at 37° C. for 45 minutes, and then at 65–68° C. for 5 minutes. Next, 24 γ of the kinased oligonucleotide is diluted with 56 γ of H$_2$O to give 2 pmole/γ.

The gapped-duplex is formed as described below, followed by annealing the oligonucleotides. The following reagents are combined in a total volume of 40 γ:8 γ5×GDB buffer, 0.50 pmole ssDNA, and 0.10 pmole HincII linearized M13 GAP RF DNA. 10 γ is removed for future use, and the remaining 30 γ is treated sequentially as follows. 100° C. for 3 minutes, 65° C. for 5 minutes, followed by cooling to room temperature for 30 minutes, and then placing the reaction mixture on ice. Next, 10 γ of gapped-duplex and 10 γ of control ungapped material is subject to electrophoresis on agarose gel to check gapped-duplex formation. If the gel shows the presence of a third band, the gapped-duplex has formed, and the kinased oligonucleotides can be annealed to the duplex by combining 16 γ of gapped-duplex reaction mixture and 4 γ of diluted kinased oligonucleotide and heating the mixture to 65° C. for 3 minutes, followed by cooling to room temperature for 20 minutes.

The heteroduplex is completed by the appropriate extension and ligation reactions consisting of combining the following reagents in a total volume of 40 γ:10 γ gapped-duplex and primer, 4 γ10×PEL buffer, 4 γ dNTP's (0.25 mM solution made from 10 mM stocks, 3 γ ATP (10 γ of 0.1 M ATP stock+1490 γ H$_2$O=0.662 mM), 17 γ H$_2$O, 1 γ Klenow (5 u/γ), and 1 γ T4 DNA ligase (0.6 Weiss u/γ), diluted stock with 1×PEL). The reaction is conducted at 16° C. for 2 hours, followed by transformation of 10 γ of the extension/ligation mixture into 200 γ of thawed competent HB2154 cells. The cells are kept at 0° C. for 30 minutes, and then 42° C. for 1.5 minutes, followed by plating various volumes of the transformation mix (e.g., 50 γ, 10 γ, etc.) with 100 γ of fresh overnight culture of HB2151 cells +3.0 γ of soft agar.

The resulting plaques are screened using the plaque hybridization procedure. While a variety of such procedures are known, a description of the preferred procedure follows. Plates are replicated onto duplicate nitrocellulose filter papers (S & S type BA-85) and the DNA fixed to the filter by sequential treatment for 5 minutes with 0.5 N NaOH plus 1.5 M NaCl; 1.0 M NaCl plus 0.5 M Tris-HCl pH 7.4; and 2×SSC (standard saline citrate). Filters are air-dried and baked at 80° C. for 2 hours, in vacuo.

The duplicate filters are prehybridized at 55° C. for 2 hours with 10 ml per filter of DNA hybridization buffer, 5×SSC, pH 7.0, 5×Denhardt's solution (polyvinylpyrrolidone, plus Ficoll and bovine serum albumin; 1×0.02% of each), 50 mM sodium phosphate buffer at pH 7.0, 5 mM EDTA, 0.1% SDS, and 100 µg/ml yeast RNA. The prehybridization buffer is removed and the samples hybridized with the appropriate kinased probe, specifically, kinased oligonucleotides as shown above, under conditions which depend on the stringency desired. About 2×10$^6$ cpm/ml total is used. Typical moderately stringent conditions employ a temperature of 42° C. plus 50% formamide for 24–36 hours with 1–5 ml/filter of DNA hybridization buffer containing probe. For higher stringencies high temperatures and shorter times are employed. The preferred hybridization conditions consists of hybridizing the probes to the filters in 5×SSC, Denhardt's solution, 50 mM NaPO$_4$, pH 7.0, 5 mM EDTA, 0.1% SDS, and 100 mg/ml yeast RNA at 10° C. below the T$_M$ of the oligonucleotide used to do the screening. Next, the filters are washed twice, 30 minutes each wash, at room temperature with 2×SSC, 0.1% SDS, then washed once with 2×SSC and 0.1% SDS at 5° C. below the T$_M$ of the oligonucleotide used to screen, and air-dried. Finally, the filters are autoradiographed at -70° C. for 36 hours. Autoradiography reveals those plaques containing the virus that carries the muteins of interest.

In addition to constructing muteins wherein valine at position 2 and/or 13 have been deleted or substituted, large deletion muteins may be produced that encompass the two predominate cleavage sites of 26 kD proTNF. A preferred embodiment mutein lacks the amino acids spanning the region -9 to +14, as shown in FIG. 1. This mutein was constructed using the materials and methods described above and the oligonucleotide, CP375 which has the following sequence (SEQ ID NO:2).

C. Protein/Peptide Inhibitors

Peptides having the following amino acid sequences are synthesized by the solid-phase method, described in detail by Merrifield, 1985), *Science,* 232:341–347: Gln-Ala-Val-Arg-Ser-Ser-Ser; (SEQ ID NO:14); (SEQ ID NO:5); (SEQ ID NO:7); (SEQ ID NO:8) and (SEQ ID NO:9). A Biosearch 9500 automated peptide machine is used with hydrogen fluoride cleavage, and purification by preparative HPLC using a Waters Delta Prep 3000 instrument, on a 15–20 µm Vydac C4 PrepPAK column.

TNF convertase inhibitory activity of these peptides is shown by performing the assay described above in the presence of varying amounts of each peptide. Gel electrophoresis and Western blotting of the reaction mixture shows an inhibition of conversion of the 26 kD proTNF to the 17 kD mature form.

EXAMPLE 7

TNF Convertase Inhibitory Activity of DCI in Mice

DCI specifically suppresses the release of TNF but not IL-6 from mouse macrophages as shown below.

Release of TNF by macrophages after stimulation by LPS is a major source of TNF. In these studies peritoneal macrophages were purified by adhesion, cultured in 24 well plates and LPS was added to induce secretion of TNF. Analysis of the kinetics of TNF release showed a maximal peak at 3 hours. DCI was then added in dimethyl sulfoxide excipient to cultures. The control cultures had DMSO alone added in equivalent concentrations. Supernatants were collected and assayed for TNF and IL-6. Results show that TNF secretion is markedly suppressed with DCI but not control excipient. In contrast the IL-6 response was not significantly altered, thus ruling out a nonspecific toxic effect (see Table 2).

Since DCI was able to specifically suppress LPS induced TNF secretion in murine macrophages the therapeutic effect of administration of DCI to mice injected with LPS was examined.

Stability and formulation studies showed that DCI when dissolved in corn oil was stable and retained serine protease inhibitor activity. Infection of DCI/oil into mice showed an LD 50% at a dose of 1 mg/ml. This represented a maximal tolerated dose of DCI that could be administered.

Figure 7:
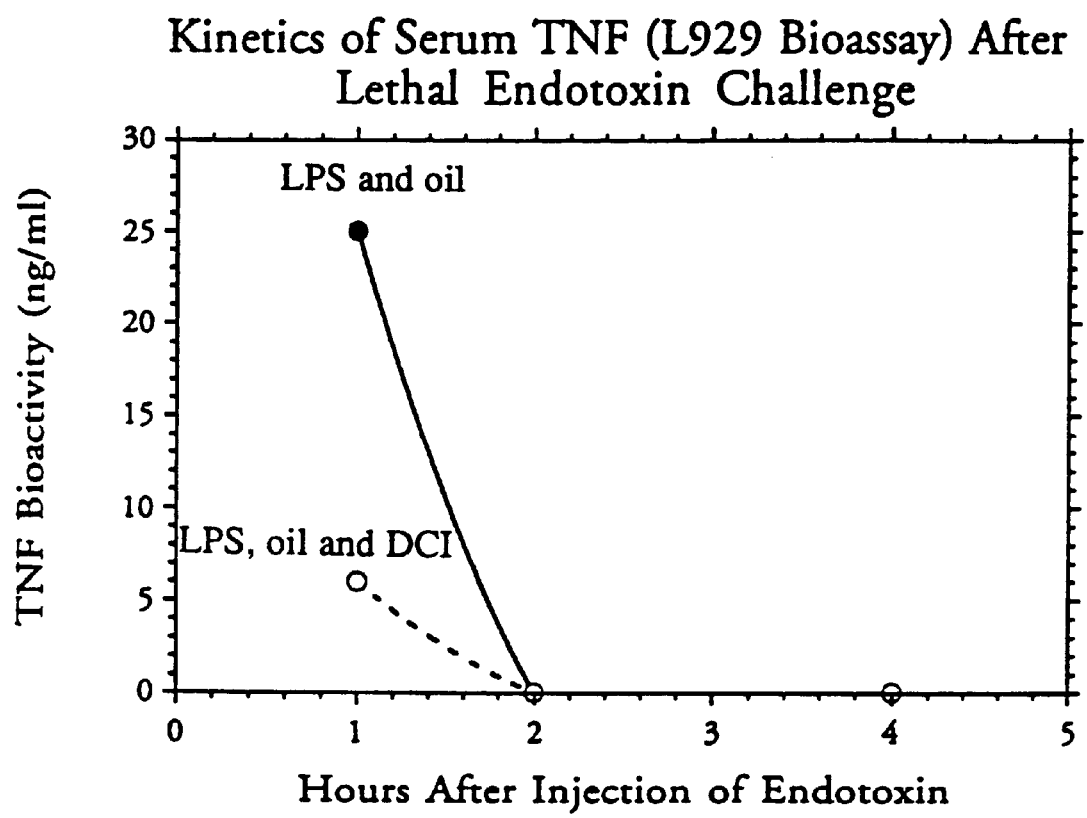
FIG. 7 shows the effect of prophylactic treatment of mice with a TNF convertase inhibitor prior to lethal injection with LPS: circulating serum TNF levels are decreased.

The kinetics of TNF and IL-6 in mice injected with a lethal dose of LPS was studied. TNF showed a sharp peak at 2 hours with return to baseline. IL-6 showed a slower gradual increase. Injection of DCI 1 hour before the LPS dose resulted in a marked inhibition of serum TNF secretion (see FIG. 7). Also, there was no delayed increase in TNF measured up to the 6-hour time point. This was true for both immunoreactive mouse TNF measured by ELISA and bioactive TNF measured by lysis of L929 cells. IL-6 levels were not reduced by this therapy.

Figure 8:
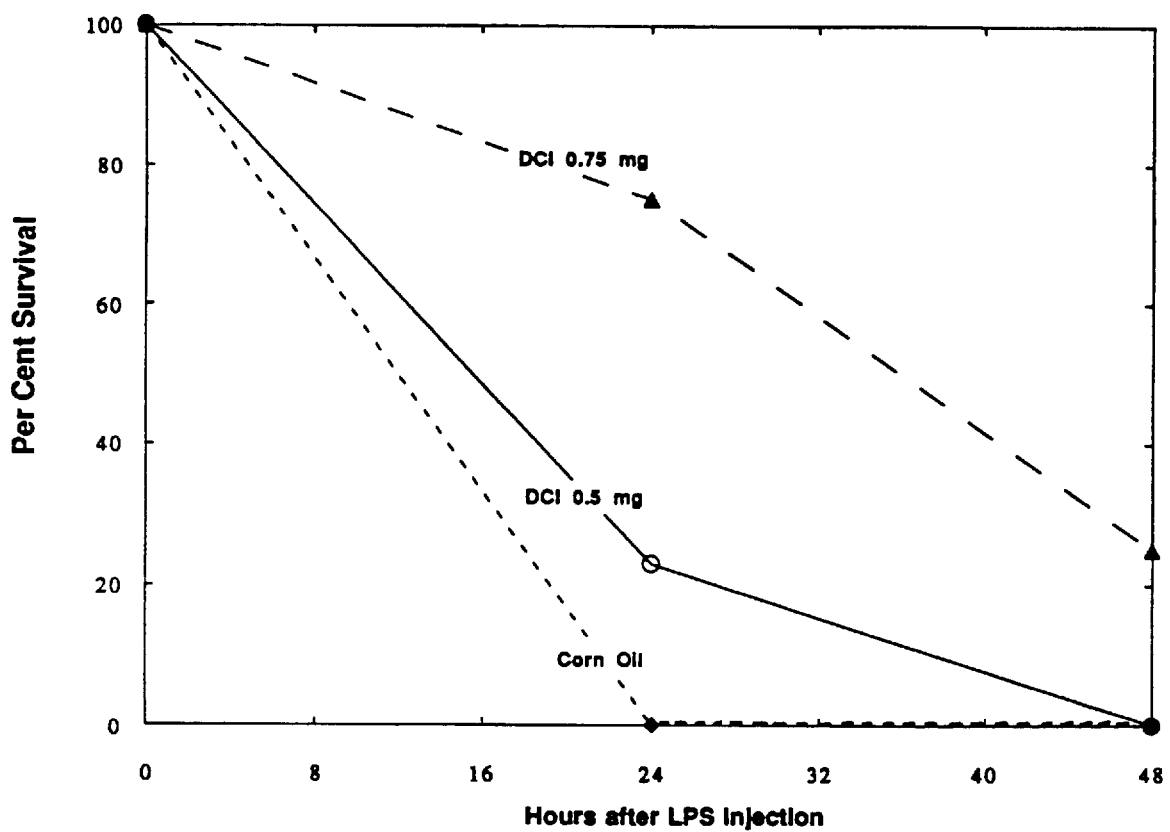
FIG. 8 shows the effect of prophylactic treatment of mice with a TNF convertase inhibitor prior to lethal injection with LPS: survival is prolonged.

The effect of DCI on survival of mice injected with a dose of LPS that results in 100% death of animals by 24 hours was also investigated. Results show that prophylactic therapy with DCI could prolong survival of mice (see FIG. 8). There was a dose response relationship noted by 0.75 mg being more effective than 0.5 mg.

In summary, these studies show that DCI is able to specifically inhibit LPS induced TNF production by murine macrophages. This specificity of inhibition of TNF could also be seen in animals injected with a lethal dose of LPS. Furthermore, the survival of animals was prolonged with DCI therapy in a dose related manner. These studies show that DCI (a serine protease inhibitor) may be beneficial in a sepsis model in prolonging survival by suppression of the systemic release of TNF.

TABLE 2

| Sample | TNF (ng/ml) | IL-6 (pg/ml) |
|---|---|---|
| DMSO control | 6.9 | 299 |
| DCI 20 ($\mu$g/ml) | 0.05 | 189 |

Adherent peritoneal macrophages (106/ml) were cultured with LPS and either DMSO or DCI DMSO. Cells were cultured for 3 hours and supernatants were collected. TNF was measured by ELISA and IL-6 by B9 bioassay.

EXAMPLE 8

Protective Effect of TNF Convertase Inhibitors in the Treatment of Sepsis

Compounds that are effective inhibitors of convertase activity are shown to prevent sepsis in a baboon model system as follows. Anti-TNF convertase antibody, murine, human, or recombinant, at a concentration of 5 mg/kg is administered in a single I.V. bolus 60 minutes before the animals are challenged with a lethal dose of *E. coli*, and 2 mg/kg simultaneously with the *E. coli* challenge. The antibody is administered in a physiologically balanced salt solution, and about $4 \times 10^{10}$ *E. coli* organisms are used. The *E. coli* dose is infused over a 2 hour period. Animals that receive the antibody are protected for at least 7 days, whereas control animals that are administered only the balanced salt solution expire within 16 to 32 hours.

Similar protection is attributable to the TNF mutein convertase inhibitors shown in Example 6. The muteins are administered at a concentration of 5 mg/kg in a single I.V. bolus 60 minutes before the animals are challenged with $4 \times 10^{10}$ *E. coli* organisms. The baboons also receive 2 mg/kg of the muteins simultaneously with the *E. coli* challenge.

Finally, the peptides shown in Example 6, that is, Gln-Ala-Val-Arg-Ser-Ser-Ser (SEQ ID NO:14) and, (SEQ ID NO:5) are tested as described above and yield similar protective effects.

EXAMPLE 9

Modelling of Human PR-3 Onto Human Elastase Crystal Structure and Use of Inhibitor-Enzyme Complex Models to Predict Novel PR-3 Inhibitors A model for the TNF convertase PR-3 was constructed by determining structural similarities shared between PR-3 and other serine proteinases. A final 3-D model of the enzyme was generated by first determining that the PR-3 sequence shared a highest degree of sequence homology with human neutrophil elastase (HNE). The crystal structure HNE (Navia et al., 1989, *PNAS* (*USA*), 86:7) was used as a scaffold to build a three dimensional representation of the PR-3 protein using the computer program Homology (Biosym, San Diego). The model was further refined by two rounds of minimization using the computer program Discover (Biosym, San Diego). The design of potential inhibitors that differentiate between HNNE and PR-3 is determined by the unique and similar amino acids found in the active sites of these enzymes. Most notably, the catalytic triad common to this class of proteinases is spatially conserved. Within the binding pocket of the PI residue (S1 site) several significant differences in amino acid side chains are proposed by the model. The following described object compound of the present invention takes into account the unique aspartic acid and leucine amino acids found within the S1 pocket of the PR-3 model and can be represented by the following general formula.

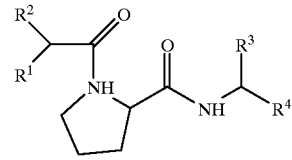

in which $R^1$, $R^2$ are lower alkyl, optionally substituted ar(lower) alkyl, cyclo(lower)alkyl(lower)alkyl or optionally substituted heterocyclic(lower)alkyl, natural amino acids, —OH, —NH2, lower alkylimino or lower alkylene;

$R^3$ is pyroyl, imidazoyl, butylamine, or ethyl-epoxide; and $R^4$ is aldehyde, diphosphonylate, ethoxycourmarinyl, chloromethyl and difluoromethyl ketonyl.

An example of a PR-3 inhibitor based on this model is Boc-Val-Pro-His-p(OPh)$_2$. Inhibition of PR-3 activity by such a compound is unexpected in light of the generally accepted belief that elastase and PR-3 selectively bind and cut after residues quite different from histidine, namely those with short aliphatic side chains such as alanine.

The present invention has been described with reference to specific embodiments. However, this application is intended to cover those changes and substitutions which may be made by those skilled in the art without departing from the spirit and the scope of the appended claims.

We claim:

1. A method of inhibiting the in vivo conversion of 26 kD pro-tumor necrosis factor (pro-TNF) to 17 kD mature tumor necrosis factor (TNF), said method comprising administering to a human patient in need of inhibition a TNF convertase inhibitor in an amount effective to substantially inhibit the conversion of said proTNF, said inhibitor comprising a composition identified as a candidate medicament by an in vitro method comprising the steps of:

a) providing a reaction mixture comprising a substrate for a human leukocyte TNF convertase and a predetermined amount of an isolated and purified TNF convertase under conditions suitable for cleavage of said substrate;

b) measuring the cleavage of said substrate by said TNF convertase in the reaction mixture of step (a);

c) providing the reaction mixture of step (a) further including a composition to be screened as an inhibitor of TNF;

d) measuring the cleavage of said substrate in step (c) by said TNF convertase;

e) comparing the cleavage of substrate in step (b) to the cleavage of substrates in step (d), whereby less cleavage in step (d) than in step (b) identifies said composition of step c) as a TNF convertase inhibitor; and f) identifying said composition from step (e) that is a TNF convertase inhibitor as a candidate medicament for inhibiting the in vivo conversion of 26 kD pro-tumor necrosis factor (proTNF) to 17 kD mature tumor necrosis factor (TNF).

2. The method of claim 1, wherein the in vivo conversion is associated with AIDS or autoimmune disease.

3. The method of claim 2 wherein the autoimmune disease is arthritis.

4. The method of claim 1, wherein the human leukocyte TNF convertase is purified from a human leukocyte cell line.

5. The method of claim 4, wherein the human leukocyte cell line is HL60.

6. A method of inhibiting the in vivo conversion of 26 kD pro-tumor necrosis factor (proTNF) to 17 kD mature tumor necrosis factor (TNF), the method comprising administering to a human patient in need of such inhibition, an treatment a therapeutically effective amount of a compound selected from the group consisting of Boc-Val-Pro-His-p(OPh)$_2$, a proTNF mutein, and an antibody having immunospecificity for a human leukocyte TNF convertase, said proTNF mutein comprising a substitution or deletion at amino acid residue positions 1 (valine) or 13 (valine), wherein said residue position 1 corresponds to residue position 1 of said mature TNF.

7. The method of claim 6, wherein the compound is a mutein of proTNF which cannot be cleaved by the TNF convertase.

8. The method of claim 7, wherein the proTNF mutein comprises a substitution or deletion at amino acid residue positions 1 (valine) or 13 (valine) with said residue position 1 corresponding to residue position 1 of said mature TNF.

9. The method of claim 6, wherein the in vivo conversion is associated with a disease that is selected from the group consisting of [sepsis,] AIDS and autoimmune disease.

10. The method of claim 6, wherein the compound is a peptide diphenyl phosphate having the formula: Boc-Val-Pro-His-p(OPh)$_2$.

11. The method of claim 6, wherein the compound is said antibody.

12. The method of claim 9, wherein said autoimmune disease is arthritis.

13. A pharmaceutical composition comprising, a therapeutically effective amount of a compound of the formula Boc-X-p(OPh)$_2$, wherein X is Val-Pro-His; and a pharmaceutically acceptable excipient.

14. A compound of the formula Boc-Val-Pro-His-p(OPh)$_2$.

* * * * *

UNITED STATES PATENT AND TRADEMARK OFFICE
CERTIFICATE OF CORRECTION

PATENT NO. : 5,998,378
DATED : December 7, 1999
INVENTOR(S) : Kriegler et al.

It is certified that error appears in the above-identified patent and that said Letters Patent is hereby corrected as shown below:

At Col. 44, line 13-14, delete "treatment a therapeutically".

At Col. 44, line 32, delete "[sepsis,]".

Signed and Sealed this

Eighteenth Day of July, 2000

Q. TODD DICKINSON

*Attest:*

*Attesting Officer*　　　*Director of Patents and Trademarks*